| (12) | United States Patent | (10) Patent No.: | US 9,039,047 B2 |
|---|---|---|---|
| | Imai | (45) Date of Patent: | May 26, 2015 |

(54) CONNECTOR ASSEMBLY

(75) Inventor: Masaomi Imai, Nakakoma-gun (JP)

(73) Assignee: TERUMO KABUSHIKI KAISHA, Shibuya-Ku, Tokyo (JP)

( * ) Notice: Subject to any disclaimer, the term of this patent is extended or adjusted under 35 U.S.C. 154(b) by 844 days.

(21) Appl. No.: 12/990,631

(22) PCT Filed: Apr. 7, 2009

(86) PCT No.: PCT/JP2009/057114
§ 371 (c)(1),
(2), (4) Date: Dec. 1, 2010

(87) PCT Pub. No.: WO2009/133754
PCT Pub. Date: Nov. 5, 2009

(65) Prior Publication Data
US 2011/0074148 A1    Mar. 31, 2011

(30) Foreign Application Priority Data

May 2, 2008  (JP) ................................ 2008-120474

(51) Int. Cl.
*F16L 21/00*       (2006.01)
*A61J 1/20*        (2006.01)
(Continued)

(52) U.S. Cl.
CPC .............. *A61J 1/2089* (2013.01); *A61J 1/2096* (2013.01); *A61J 2001/2037* (2013.01);
(Continued)

(58) Field of Classification Search
USPC ................... 285/331, 361, 396, 402; 604/414
See application file for complete search history.

(56) References Cited

U.S. PATENT DOCUMENTS

2002/0066715 A1   6/2002 Niedospial, Jr.
2003/0199847 A1  10/2003 Akerlund et al.
(Continued)

FOREIGN PATENT DOCUMENTS

| JP | 11-033124 A | 2/1999 |
| JP | 2003-175115 A | 8/2003 |
| JP | 2004-517673 A | 6/2004 |

(Continued)

OTHER PUBLICATIONS

International Search Report (PCT/ISA/210) issued on Jul. 21, 2009, by Japanese Patent Office as the International Searching Authority for International Application No. PCT/JP2009/057114.
(Continued)

*Primary Examiner* — Daniel P Stodola
*Assistant Examiner* — Gwendolyn Driggers
(74) *Attorney, Agent, or Firm* — Buchanan Ingersoll & Rooney PC

(57) ABSTRACT

A connector assembly includes a first connector having an outer tube and an inner tube, the outer tube being equipped with a pin having a first flow path, the inner tube being equipped with a first valve element opening and closing the first flow path; a second connector having a second flow path and a second valve element for opening and closing the second flow path; a locking device interconnecting, in an assembled state in which the first and second connectors are assembled together, the inner tube and the second connector; and an unlocking device for unlocking the connection between the inner tube and the second connector effected by the locking device. The first and second flow paths are interconnected in the assembled state. In this interconnected state, the connection between the inner tube and the second connector by the locking device cannot be unlocked by the unlocking device.

10 Claims, 19 Drawing Sheets

(51) Int. Cl.
*A61M 5/162* (2006.01)
*A61M 39/04* (2006.01)
*A61M 39/26* (2006.01)
*A61M 39/10* (2006.01)
*A61M 39/12* (2006.01)

(52) U.S. Cl.
CPC ........ *A61J 2001/2058* (2013.01); *A61M 5/162* (2013.01); *A61M 39/045* (2013.01); *A61M 39/1011* (2013.01); *A61M 39/12* (2013.01); *A61M 39/26* (2013.01); *A61M 2039/1016* (2013.01); *A61M 2039/1077* (2013.01); *A61M 2039/267* (2013.01)

(56) References Cited

U.S. PATENT DOCUMENTS

2006/0142735 A1    6/2006   Whitley
2009/0069783 A1*   3/2009   Ellstrom et al. .............. 604/415

FOREIGN PATENT DOCUMENTS

JP     2005-522282 A     7/2005

OTHER PUBLICATIONS

Extended European Search Report issued Dec. 19, 2012 by the European Patent Office in European Application No. 09738691.6 (4 pages).

* cited by examiner

CONNECTOR ASSEMBLY

TECHNICAL FIELD

The present invention relates to a connector assembly.

BACKGROUND ART

Normally, a medical agent which is dangerous if a medical care worker touches it by mistake, such as carcinostatics, immunosuppressants, etc. is contained in a powdery state in a vial container (medical agent container) having a mouth portion sealed with a rubber stopper.

In taking the medical agent out of such a vial container, operations as follows are carried out.

First, the mouth portion of the vial container and a mouth portion of a syringe into which dissolving liquid has been portioned out are connected to each other through a connector (see Patent Document 1). Next, in this connected state, the dissolving liquid is injected from the syringe into the vial container. Then, by such an operation as a pumping operation or shaking of the vial container, the medical agent is dissolved uniformly in the dissolving liquid. Subsequently, the dissolving liquid with the medical agent dissolved therein (hereinafter referred to as "liquid medical agent") is taken out into the syringe by suction.

The connector described in Patent Document 1 that is used for such operations includes a hollow needle having a sharp needle point at its distal end, a hub (connecting portion) for supporting the hollow needle, and a cover member for covering the needle point. The cover member can be moved along the longitudinal direction of the hollow needle, and can be displaced into a first position for covering the needle point and a second position for letting the needle point exposed. Further, the connector is equipped with a stopper (safety latch) which inhibits the cover member from being unwillingly moved from the first position to the second position. The connector having such a constitution can be used in a state (hereinafter referred to as "used state") wherein, for example, the hub is connected (mounted) to the syringe, the cover member is put into the second position by operating the stopper, and the rubber stopper of the vial container is pierced through by the hollow needle. In the used state, the inside of the syringe and the inside of the vial container communicate with each other through the connector (hollow needle).

However, the connector disclosed in Patent Document 1 has a problem in that if such force as to pull the hollow needle from the rubber stopper of the vial container acts in the used state, then the hollow needle would be easily pulled out of the rubber stopper of the vial container. In this case, the liquid medical agent may be scattered from the exposed needle point, and adhere to a medical care worker or the like, or the medical care worker may be punctured with the needle point by mistake. Thus, there has been a problem that the liquid medical agent cannot be transferred safely and reliably through the connector.

Patent Document 1: Japanese Laid-Open Patent Publication No. 2005-522282 (PCT)

DISCLOSURE OF INVENTION

The object of the present invention is to provide a connector assembly which is capable of transferring liquid safely and reliably from a first connector side to a second connector side or in the opposite direction.

In order to achieve the above object, according to the present invention, there is provided a connector assembly including:

a first connector having an outer tube having a tubular shape and including a hollow pin having a lumen provided in an inner side thereof and functioning as a first flow path through which liquid can pass, and an inner tube having a tubular shape and including a first valve body made of an elastic material for opening and closing the first flow path, the inner tube being disposed for rotation around an axis thereof in the outer tube and for movement along the direction of the axis;

a second connector including a tubular second connector main body having a lumen which functions as a second flow path through which liquid can pass, and a second valve body disposed in the second connector main body and made of an elastic material for opening and closing the second flow path;

locking means for connecting the inner tube and the second connector main body in an assembled state in which the first connector and the second connector are assembled; and unlocking means for releasing the connection between the inner tube and the second connector main body by the locking means, wherein the assembled state includes:

a first state in which the inner tube and the second connector main body are connected by the locking means, and the inner tube and the second connector main body are rotatable around the axis of the outer tube with respect to the outer tube but are not movable in an axial direction while the first flow path is closed by the first valve body and the second flow path is closed by the second valve body;

a second state which is established by rotating the inner tube and the second connector main body around the axis of the outer tube with respect to the outer tube from the first state, and in which the inner tube and the second connector main body are movable in the axial direction with respect to the outer tube, and a third state which is established by moving the inner tube and the second connector main body in the axial direction with respect to the outer tube from the second state so as to approach thereto, and in which the pin is inserted through the first valve body and the second valve body to communicate the first flow path and the second flow path with each other, and wherein the connection between the inner tube and the second connector main body by the locking means is capable of being released by the unlocking means when the connector assembly is in the first state, whereas the connection is not capable of being released by the unlocking means when the connector assembly is in any of the second state and the third state.

Consequently, the connector assembly can assume, in the assembled state in which the first connector and the second connector are assembled, the first state, the second state and the third state. In the third state, the first flow path and the second flow path are communicated with each other, and liquid can be transferred reliably from the first connector side to the second connector side or in the opposite direction through the first flow path and the second flow path communicated with each other.

Further, in the third state, it is impossible to release the assembled state of the first connector and the second connector. Consequently, the connector assembly in the assembled state can be prevented reliably from being disassembled inadvertently, and therefore, liquid can be transferred safely through the connector assembly.

Preferably, in the connector assembly of the present invention, a wall portion of one of the outer tube and the inner tube has a groove portion formed therein and having a transverse groove formed along a circumferential direction thereof and a longitudinal groove formed along an axial direction thereof and communicating with the transverse groove while a wall portion of the other of the outer tube and the inner tube has a projection formed so as to project thereon and inserted in the groove portion such that the projection moves along the transverse groove when the inner tube rotates around the axis thereof with respect to the outer tube and such that the projection moves along the longitudinal groove when the inner tube moves along the axial direction thereof with respect to the outer tube.

Consequently, the connector assembly can be operated to the first state, the second state and the third state smoothly.

Preferably, in the connector assembly of the present invention, when the connector assembly is in the first state, the projection is positioned at an end portion of the transverse groove on the opposite side of the longitudinal groove, and when the connector assembly is in the second state, the projection is positioned at an intersection between the transverse groove and the longitudinal groove, whereas when the connector assembly is in the third state, the projection is positioned at an end portion of the longitudinal groove on the opposite side of the transverse groove.

Consequently, the connector assembly can be operated to the first state, the second state and the third state smoothly.

Preferably, in the connector assembly of the present invention, the groove portion has the transverse groove disposed at each of opposite end portions of the longitudinal groove.

Consequently, the third state can be maintained.

Preferably, in the connector assembly of the present invention, the locking means comprises a first engaging portion provided on an outer circumferential portion of the inner tube and a second engaging portion provided on an inner circumferential portion of the second connector main body for engaging with the first engaging portion.

Consequently, when liquid flows down through the connector assembly in the assembled state, the connector assembly can be prevented reliably from being disassembled into the first connector and the second connector. Therefore, transferring of liquid can be carried out safely and reliably.

Preferably, in the connector assembly of the present invention, each of the first valve body and the second valve body has a portion of a columnar shape, and end faces of the portions closely contact liquid-tightly with each other in the assembly state.

Consequently, liquid which passes through the connector assembly in the assembled state can be prevented reliably from leaking to the outside.

Preferably, in the connector assembly of the present invention, each of the first valve body and the second valve body has a portion of a columnar shape, and the portion having a slit formed therein so as to extend through the portion in the axial direction.

Consequently, liquid which passes through the connector assembly in the assembled state can be prevented more reliably from leaking to the outside.

Preferably, in the connector assembly of the present invention, when the connector assembly is in the third state, the first valve body and the second valve body press against and contact with an outer circumferential portion of the pin.

Consequently, the connector assembly is prevented reliably from inadvertently returning to the second state.

Preferably, in the connector assembly of the present invention, the outer tube has a connecting portion to be connected, by threaded engagement, to a liquid container in which liquid can be contained, and a direction of rotation of the liquid container when the liquid container is to be connected to the outer tube, is opposite to a direction of rotation in which the inner tube and the second connector main body rotate around the axis with respect to the outer tube upon transition from the first state to the second state.

Consequently, when the inner tube and the second connector are rotated with respect to the outer tube, the threaded engagement between the connecting portion of the outer tube and the liquid container is prevented reliably from being loosened (released). Therefore, during use of the connector assembly in the assembled state, the liquid container is prevented from being removed inadvertently from the first connector.

Preferably, in the connector assembly of the present invention, the pin is positioned on an inner side of the inner tube; and a ring-shaped packing made of an elastic material is disposed between an outer circumferential portion of the pin and an inner circumferential portion of the inner tube.

Consequently, the liquid tightness (air tightness) of the first flow path can be maintained reliably, and liquid which passes through the first flow path is prevented reliably from leaking from the connector assembly in the assembled state.

Preferably, in the connector assembly of the present invention, the second flow path is formed so that a direction in which liquid flows through the second flow path is changed to the opposite direction in the proximity of the second valve body.

Consequently, even if air bubbles exist in liquid which passes through the second flow path, they are prevented from remaining in the second flow path.

Preferably, in the connector assembly of the present invention, the groove portion is formed so as to extend through the wall portion of the outer tube, and the projection is formed on the inner tube and exposed through the groove portion.

Consequently, the position of the projection with respect to the groove portion can be visually confirmed, and therefore, it can be grasped whether the connector assembly is placed in the first state, the second state or the third state.

Preferably, in the connector assembly of the present invention, the inner tube has two missing portions formed in the wall portion thereof along the axial direction thereof and an elastic piece formed between the missing portions, and the first engaging portion is positioned on the elastic piece.

Consequently, the first engaging portion of the inner tube in the assembled state can be engaged with the second connector.

Preferably, in the connector assembly of the present invention, the unlocking means comprises a pressing portion provided on the outer tube and pressing the elastic piece toward the inner side when the connector assembly is in the first state.

Consequently, when the elastic piece is operated to be pressed, the operation can be carried out easily and reliably.

Preferably, in the connector assembly of the present invention, when the connector assembly is in any of the second state and the third state, the elastic piece is retracted to a position at which the elastic piece is not pressed by the pressing portion.

Consequently, when liquid flows down through the connector assembly in the assembled state, the connector assembly is prevented reliably from being disassembled into the first connector and the second connector. Therefore, transferring of liquid can be carried out safely and reliably.

Preferably, in the connector assembly of the present invention, the pressing portion forms part of the wall portion of the outer tube.

Consequently, the constitution of the outer tube is simplified in comparison with that in a case in which the pressing portion is formed separately from the wall portion of the outer tube.

Preferably, in the connector assembly of the present invention, the slit of the first valve body and the slit of the valve body have a straight line shape, and directions in which the slits of the first valve body and of the second valve body are formed are not the same with each other in the assembled state.

Consequently, when the third state is entered, the liquid tightness in the proximity of the end face of the first valve body and the end face of the second valve body is maintained reliably.

Preferably, the connector assembly of the present invention further includes positioning means for carrying out positioning of the inner tube and the second connector main body when the inner tube and the second connector main body are connected.

Consequently, when the first connector and the second connector are connected to each other, the connecting operation can be carried out reliably.

Preferably, the connector assembly of the present invention further includes blocking means for blocking the inner tube from rotating around the axis thereof with respect to the outer tube in the first state.

Consequently, the first state is maintained reliably.

Preferably, in the connector assembly of the present invention, the second connector is connected to an end portion of a tube or a mouth portion of a liquid container in which liquid can be contained.

Consequently, liquid can be transferred safely and reliably from the first connector side to the second connector side or in the opposite direction.

BEST MODE FOR CARRYING OUT THE INVENTION

In the following, a connector assembly of the present invention is described in detail based on preferred embodiments shown in the accompanying drawings.

First Embodiment

Figure 1:
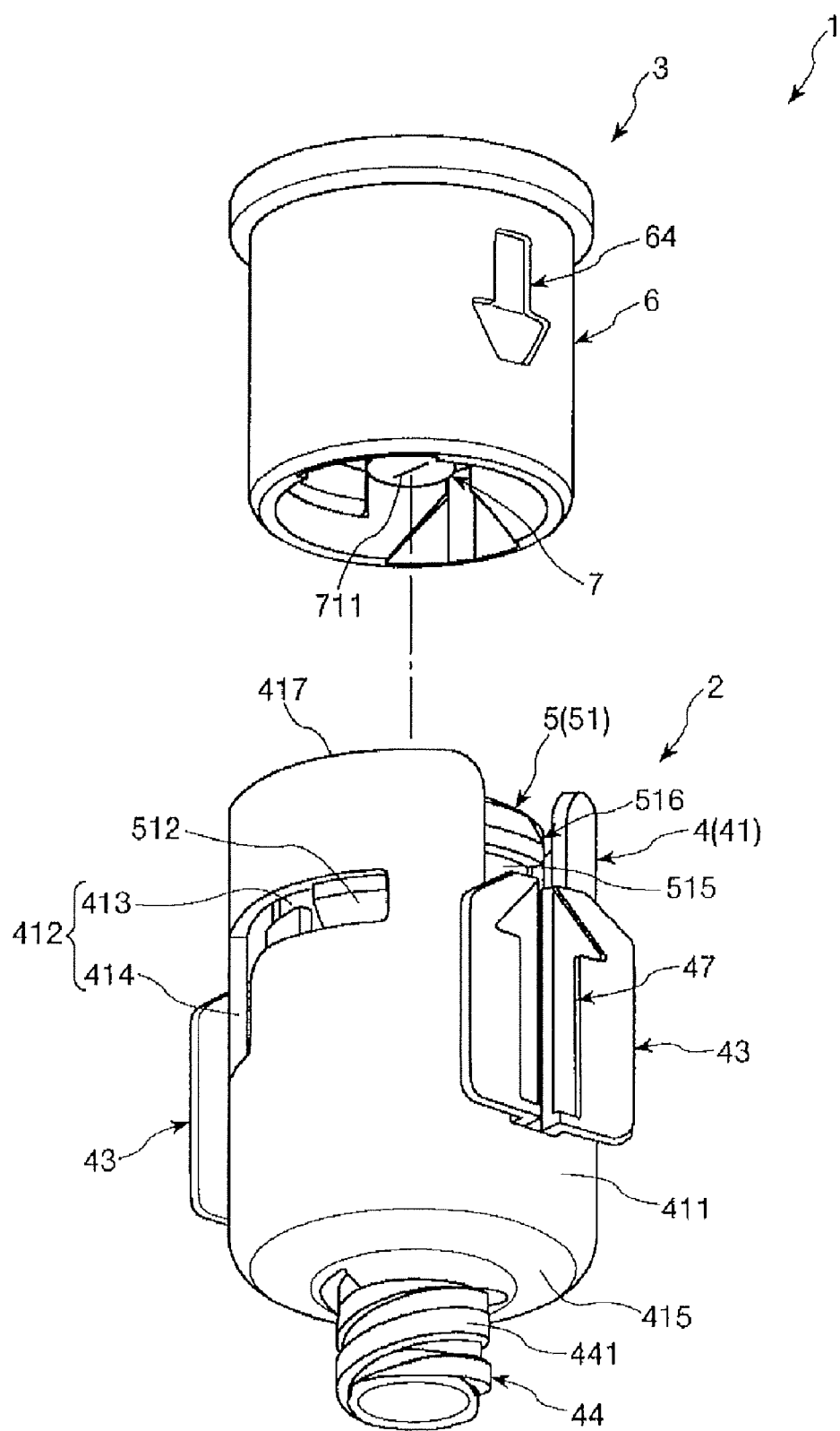
FIG. 1 is an exploded perspective view of a connector assembly (first embodiment) of the present invention.
Figure 2:
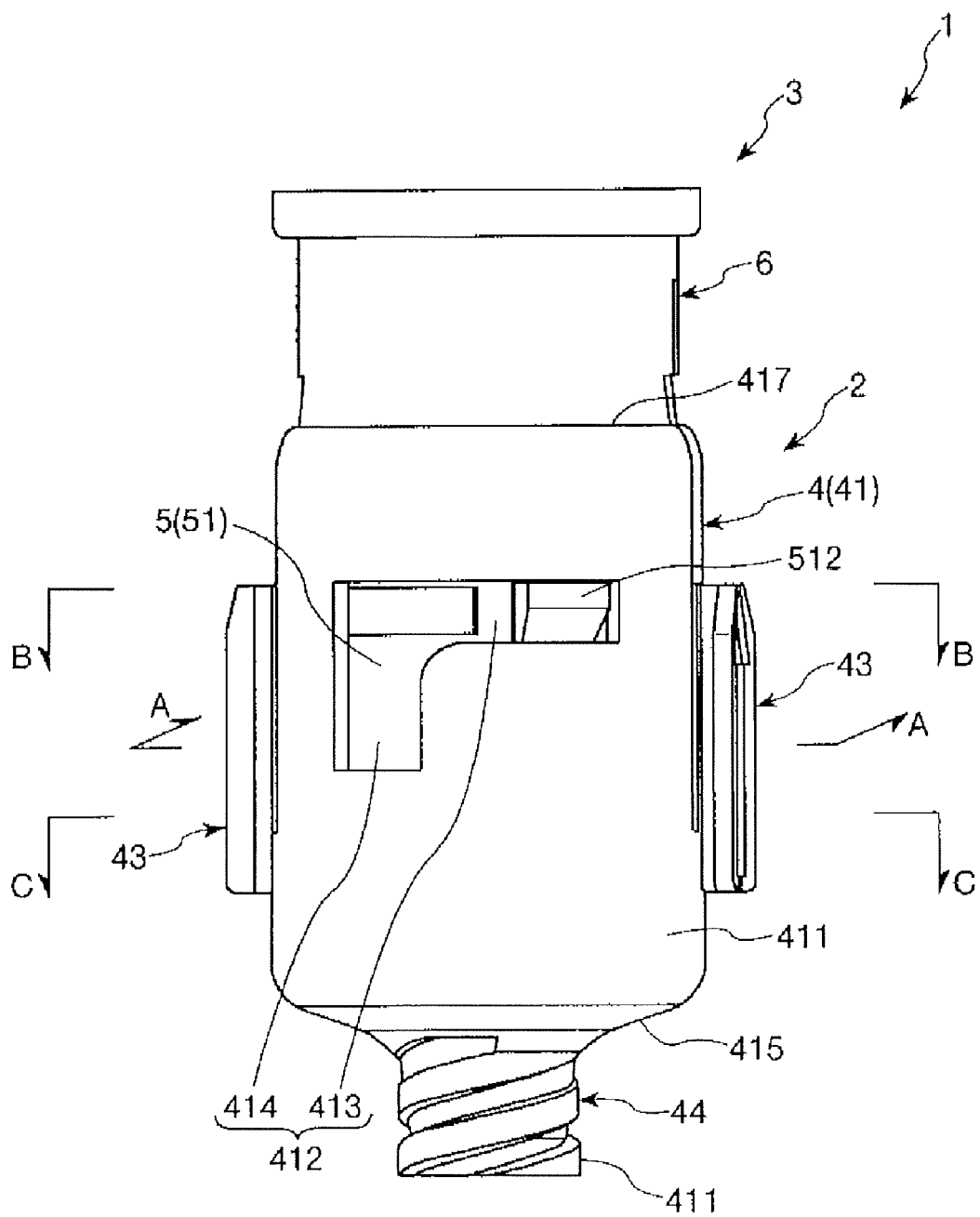
FIG. 2 is a perspective view illustrating a first state of the connector assembly (first embodiment) of the present invention.
Figure 3:
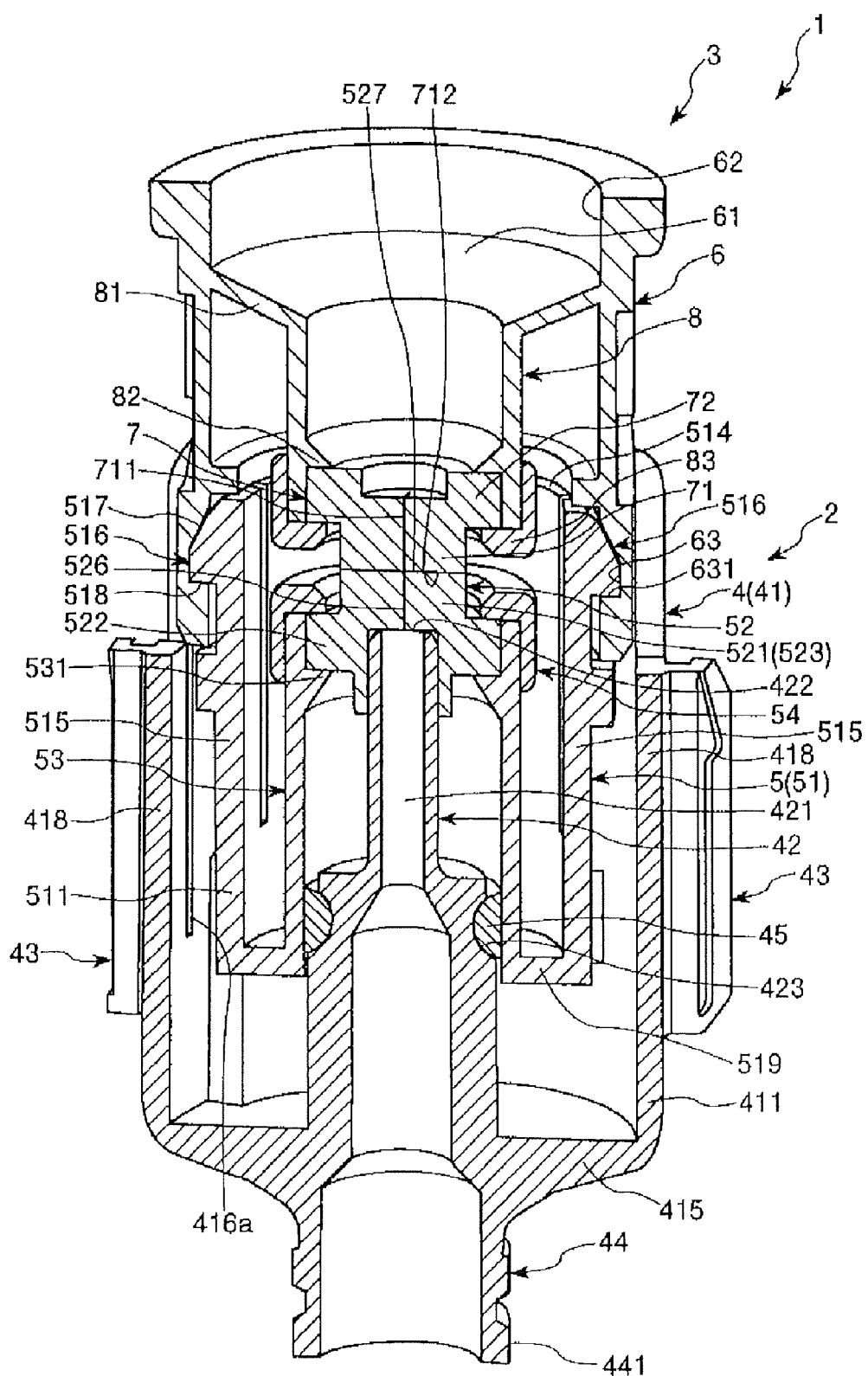
FIG. 3 is a sectional view taken along line A-A in FIG. 2.
Figure 4:
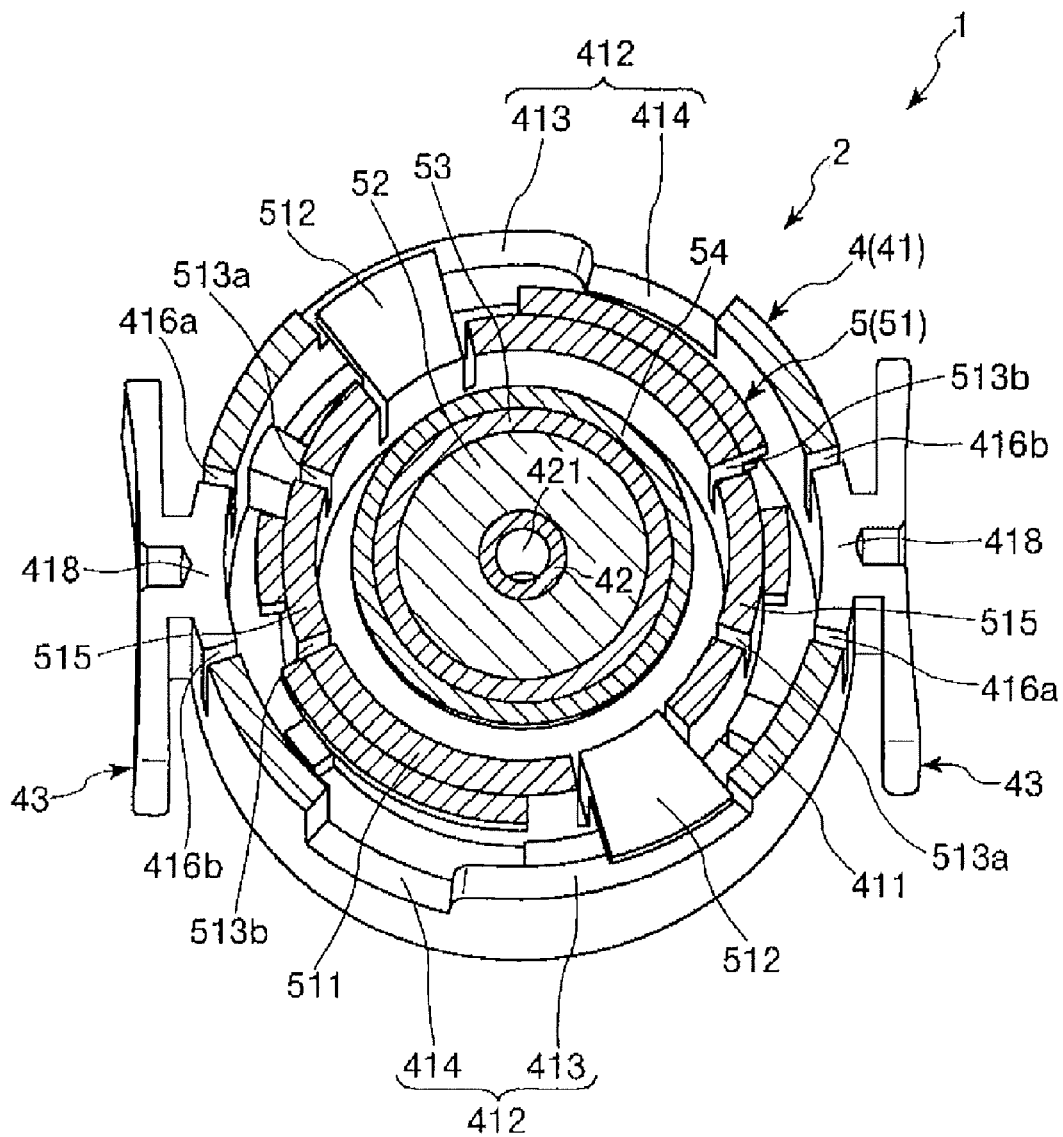
FIG. 4 is a sectional view taken along line B-B in FIG. 2.
Figure 5:
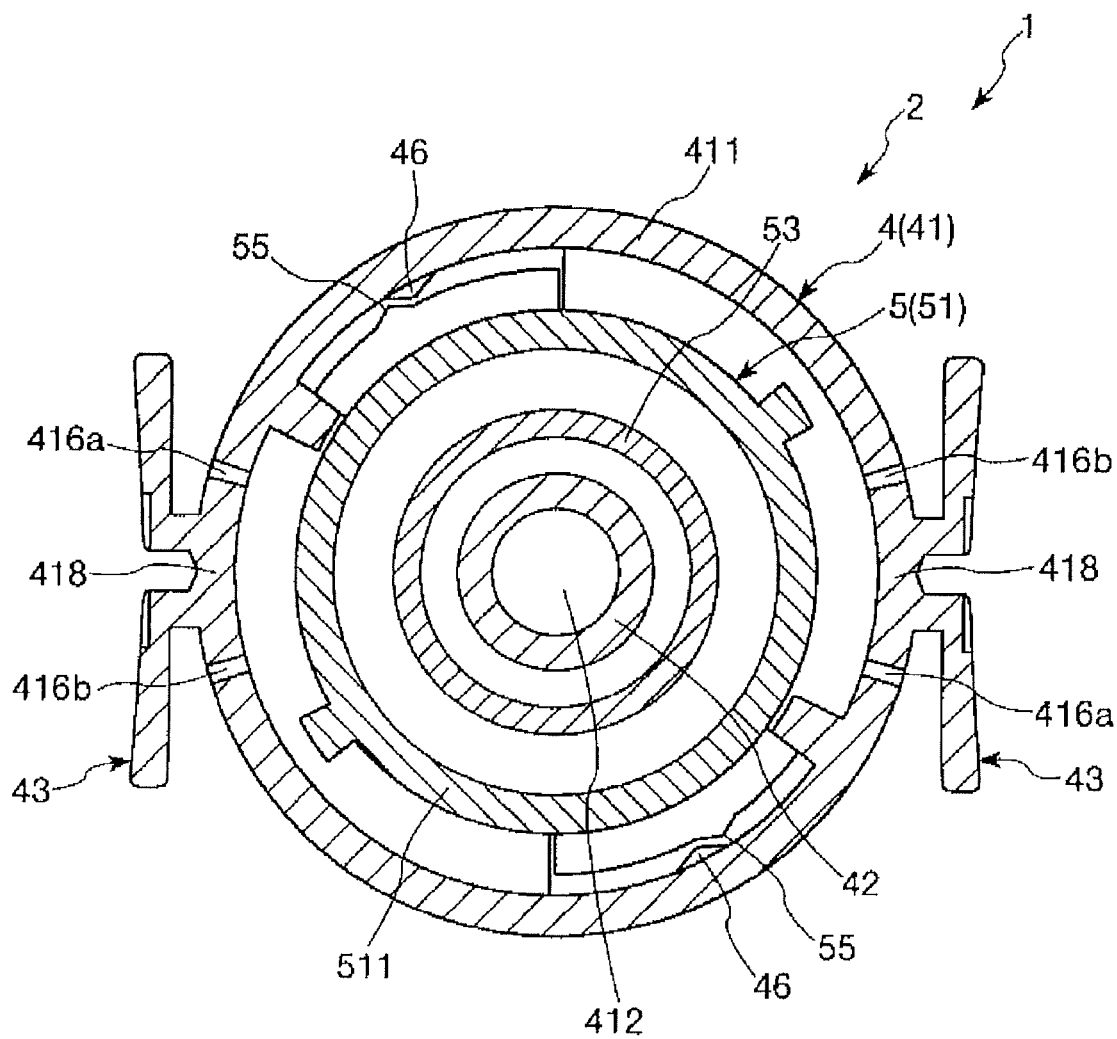
FIG. 5 is a sectional view taken along line C-C in FIG. 2.
Figure 6:
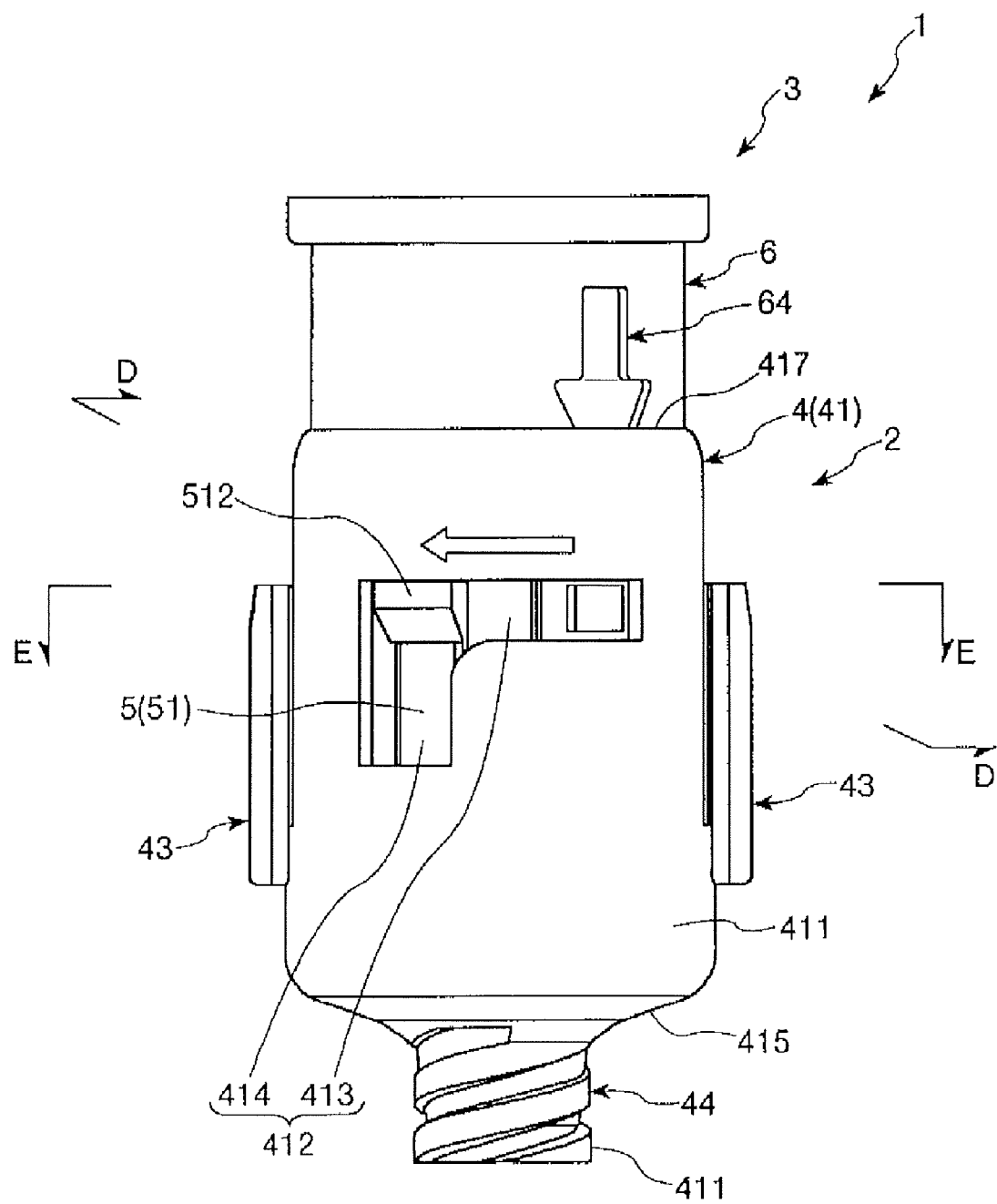
FIG. 6 is a perspective view illustrating a second state of the connector assembly (first embodiment) of the present invention.
Figure 7:
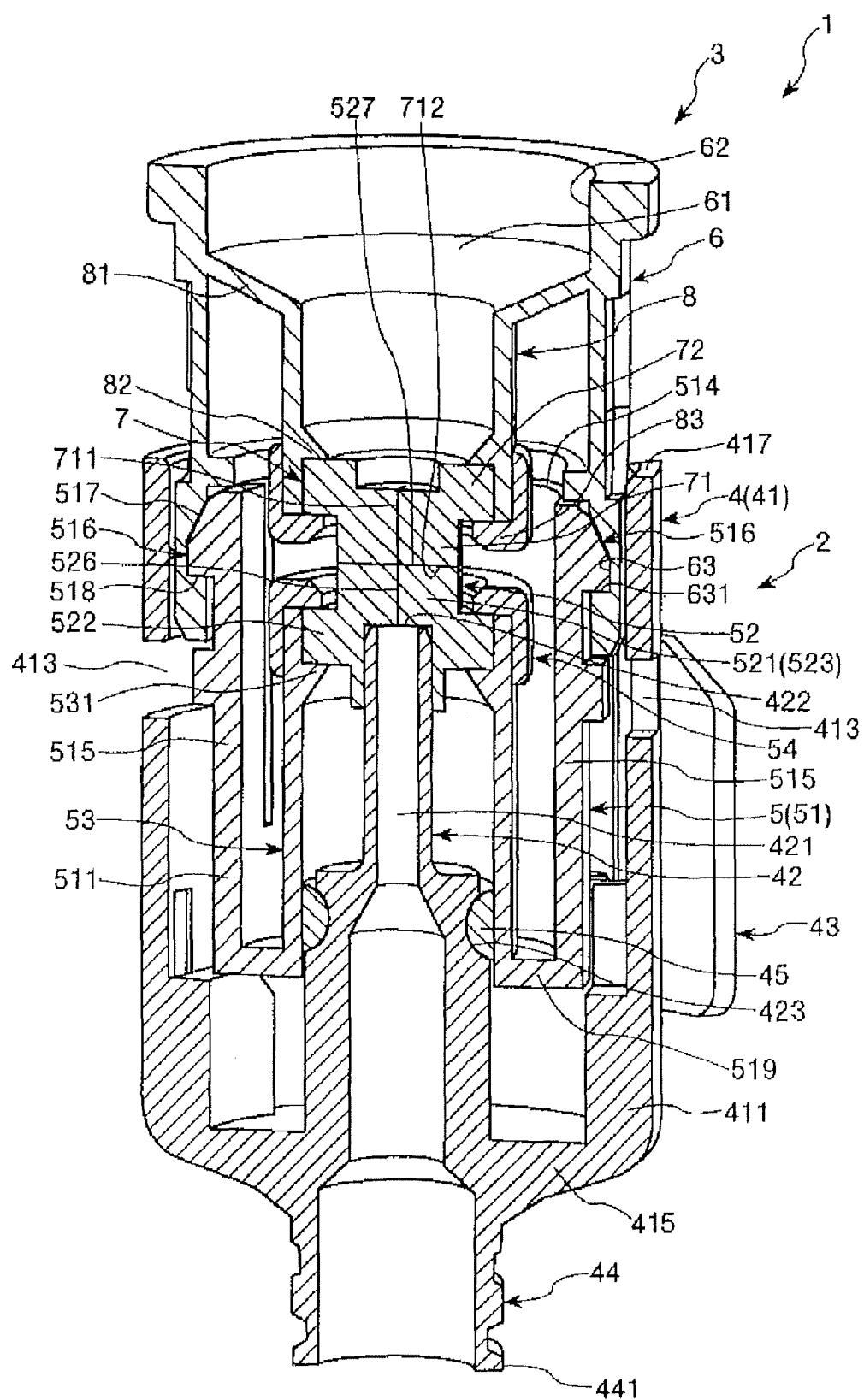
FIG. 7 is a sectional view taken along line D-D in FIG. 6.
Figure 8:
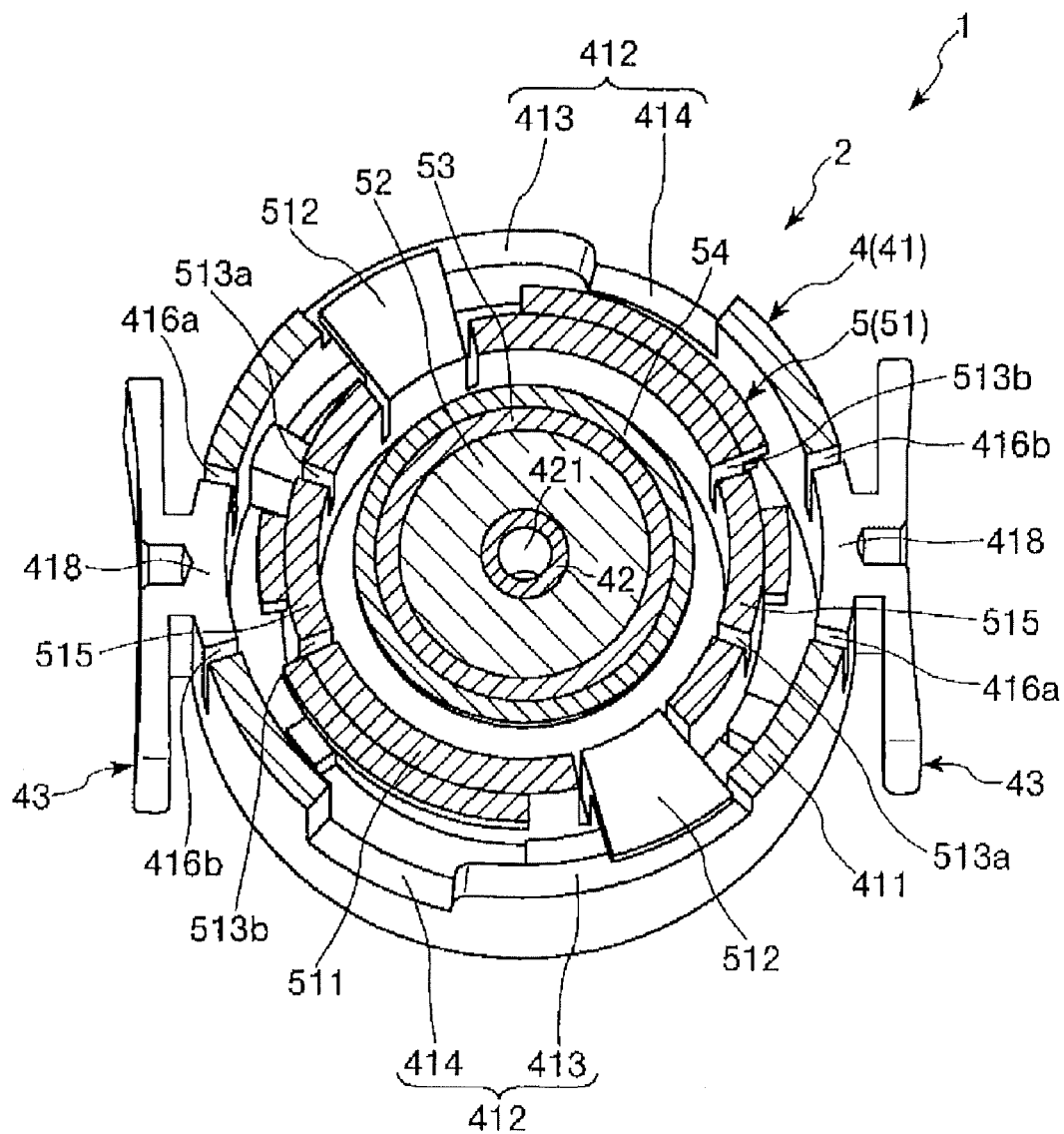
FIG. 8 is a sectional view taken along line E-E in FIG. 6.
Figure 9:
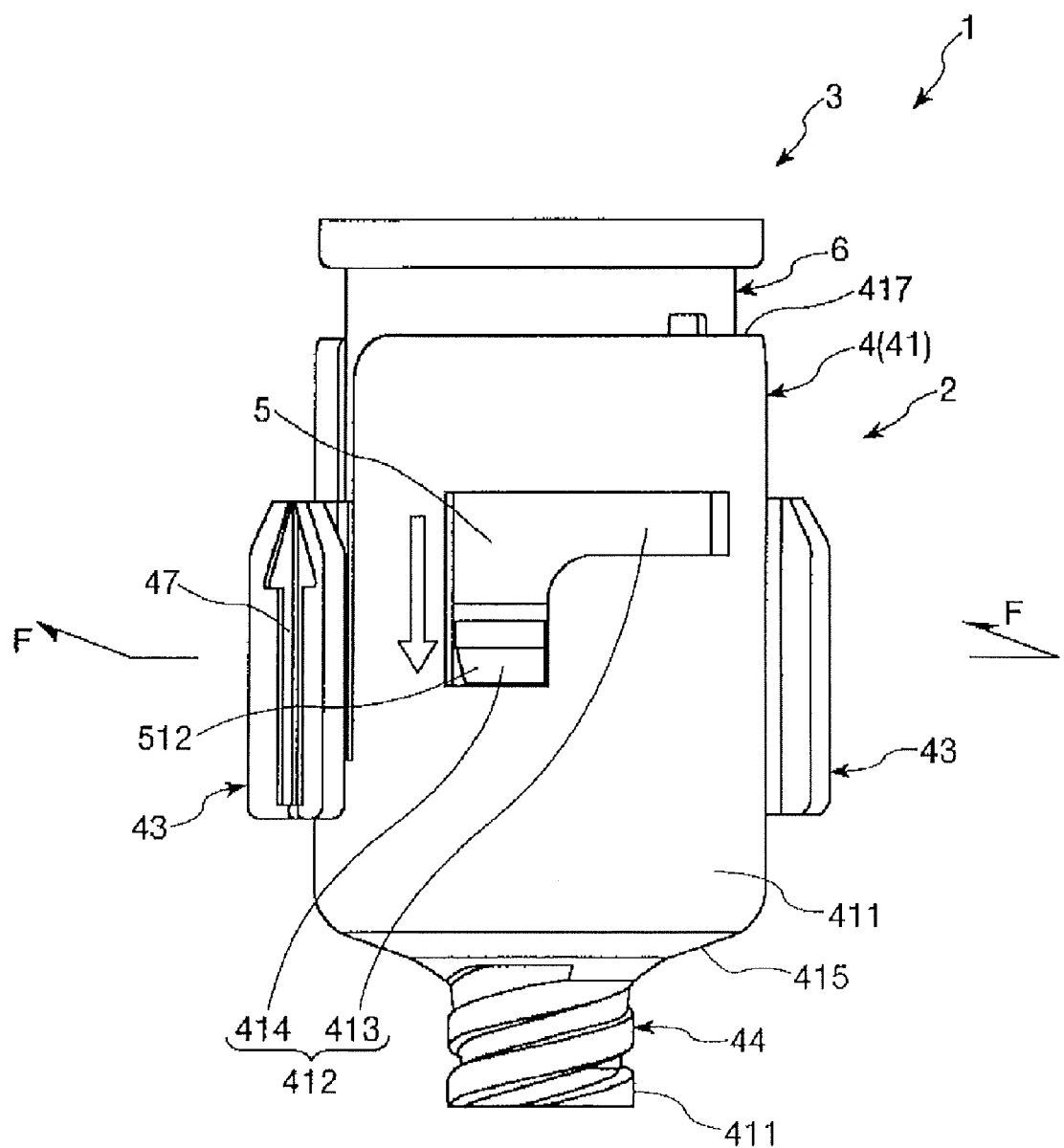
FIG. 9 is a perspective view illustrating a third state of the connector assembly (first embodiment) of the present invention.
Figure 10:
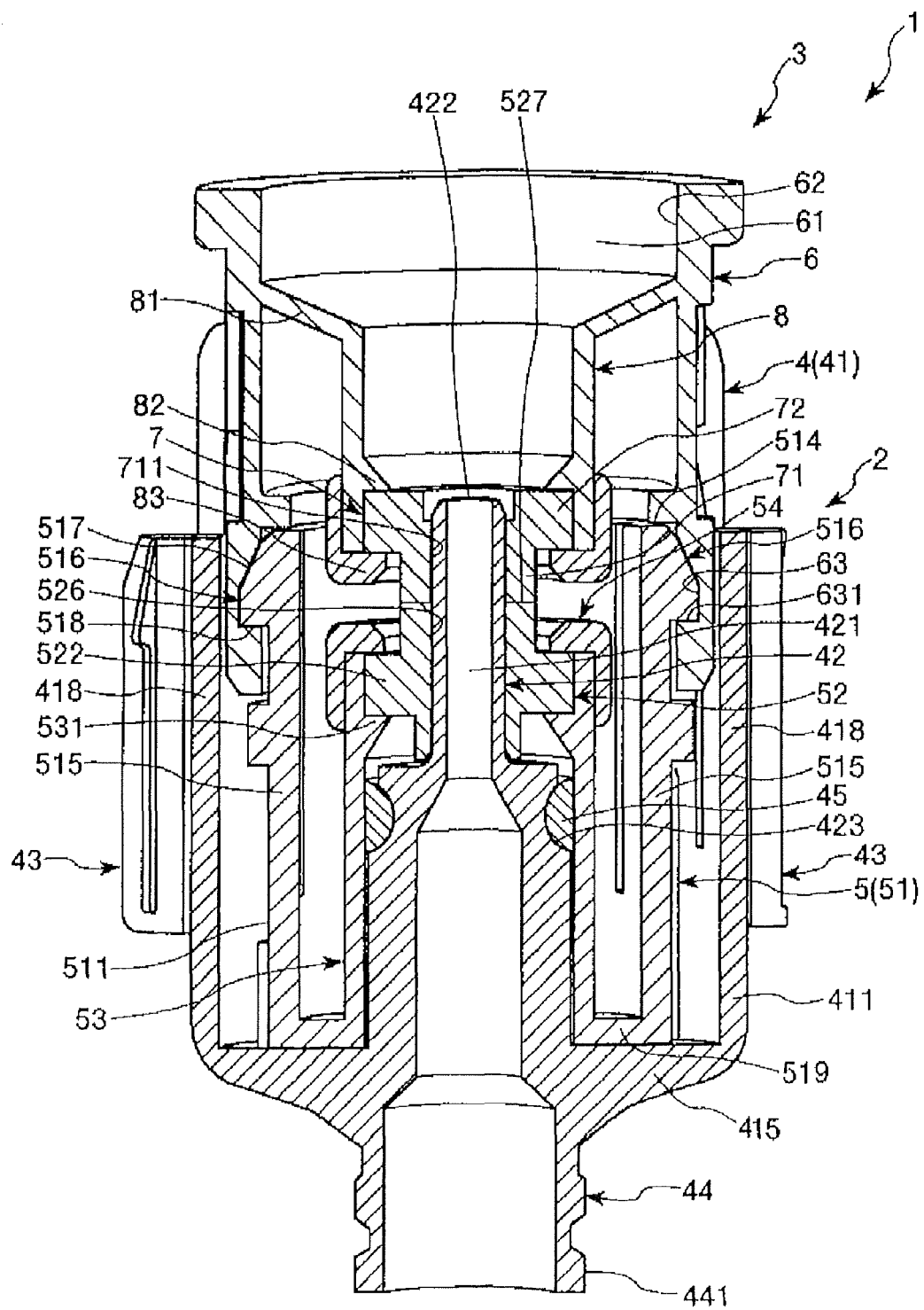
FIG. 10 is a sectional view taken along line F-F in FIG. 9.
Figure 11:
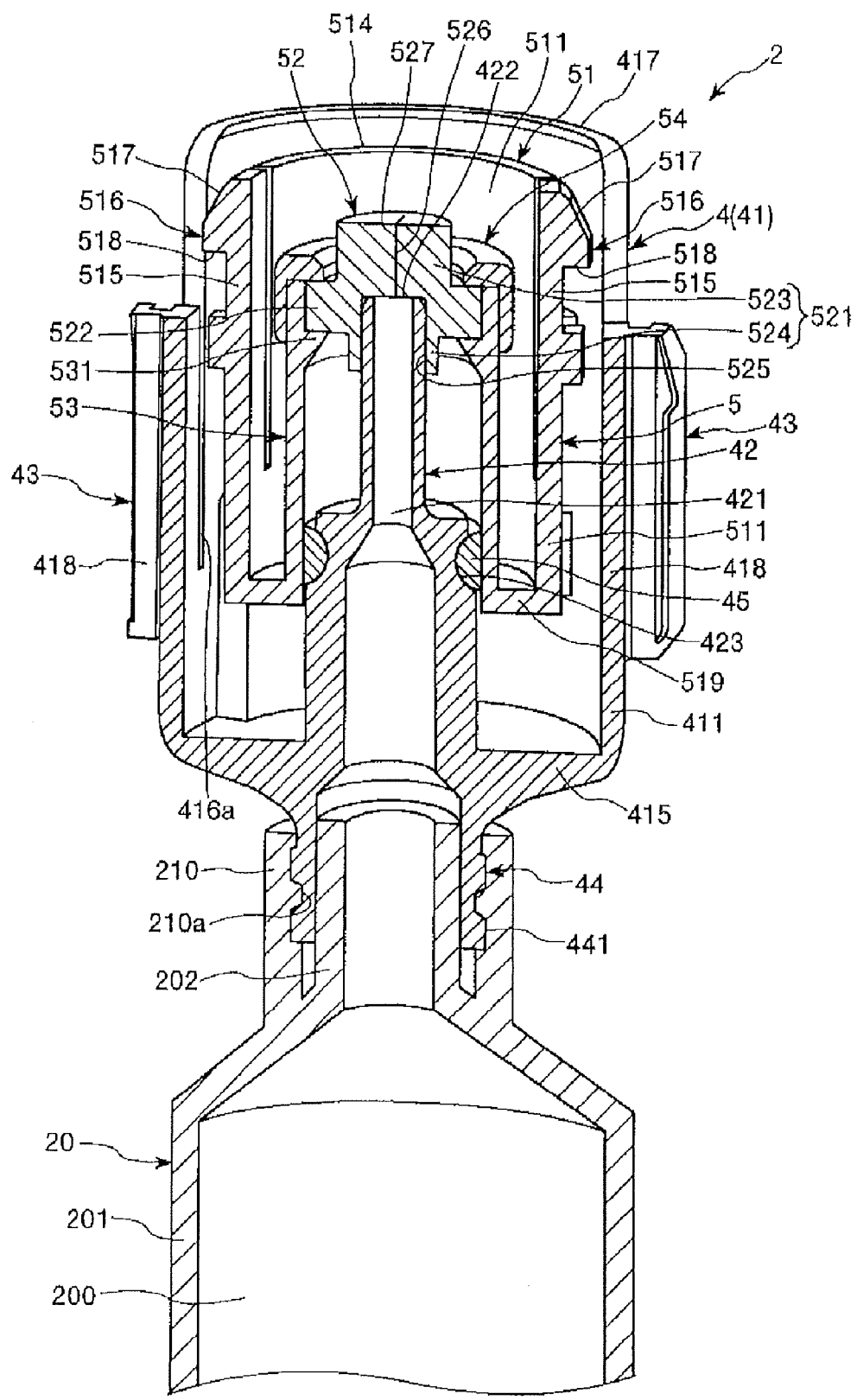
FIG. 11 is a vertical sectional perspective view showing a first connector in the connector assembly (first embodiment) of the present invention.
Figure 12:
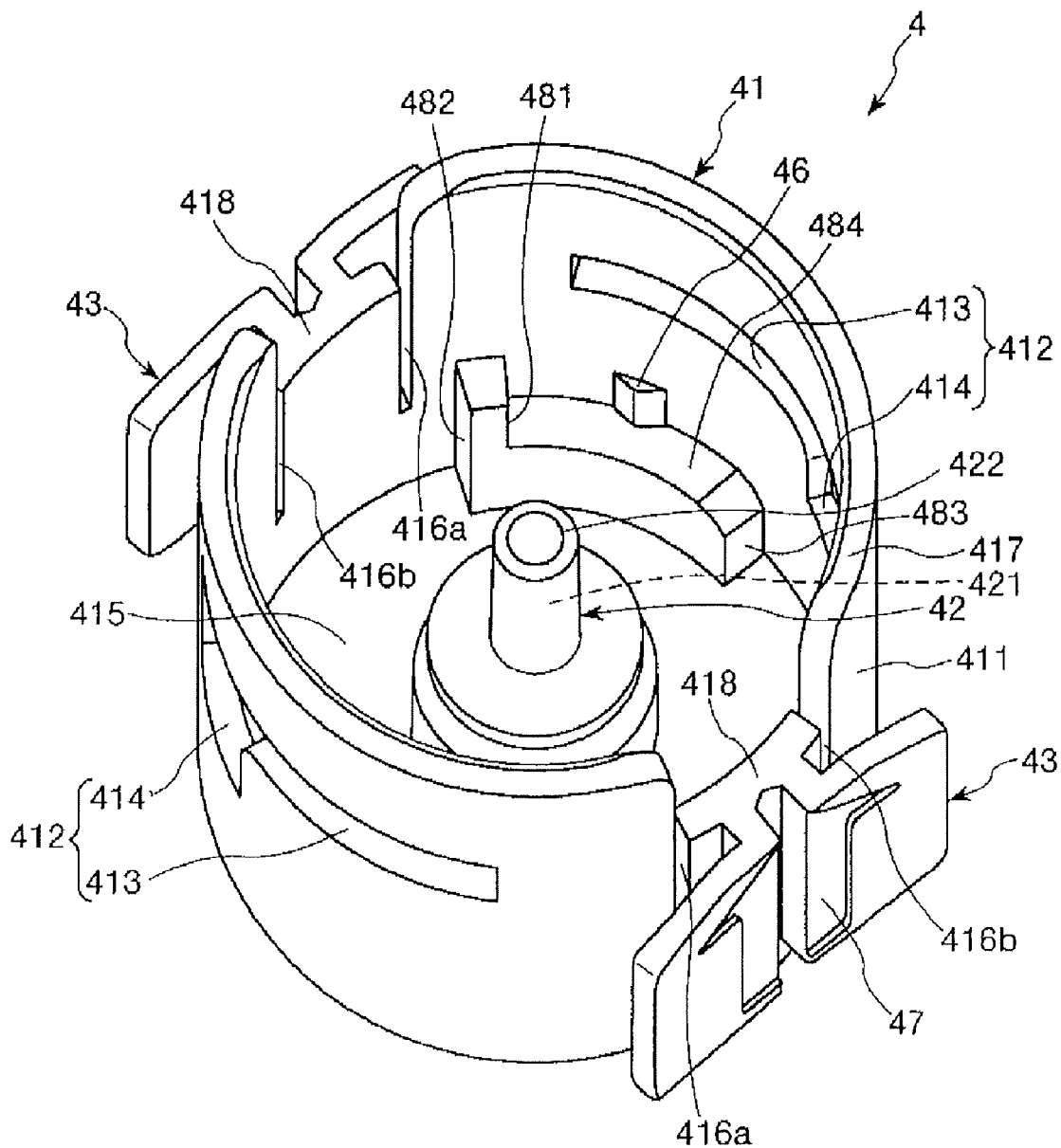
FIG. 12 is a perspective view showing an outer tube of the first connector shown in FIG. 11.
Figure 13:
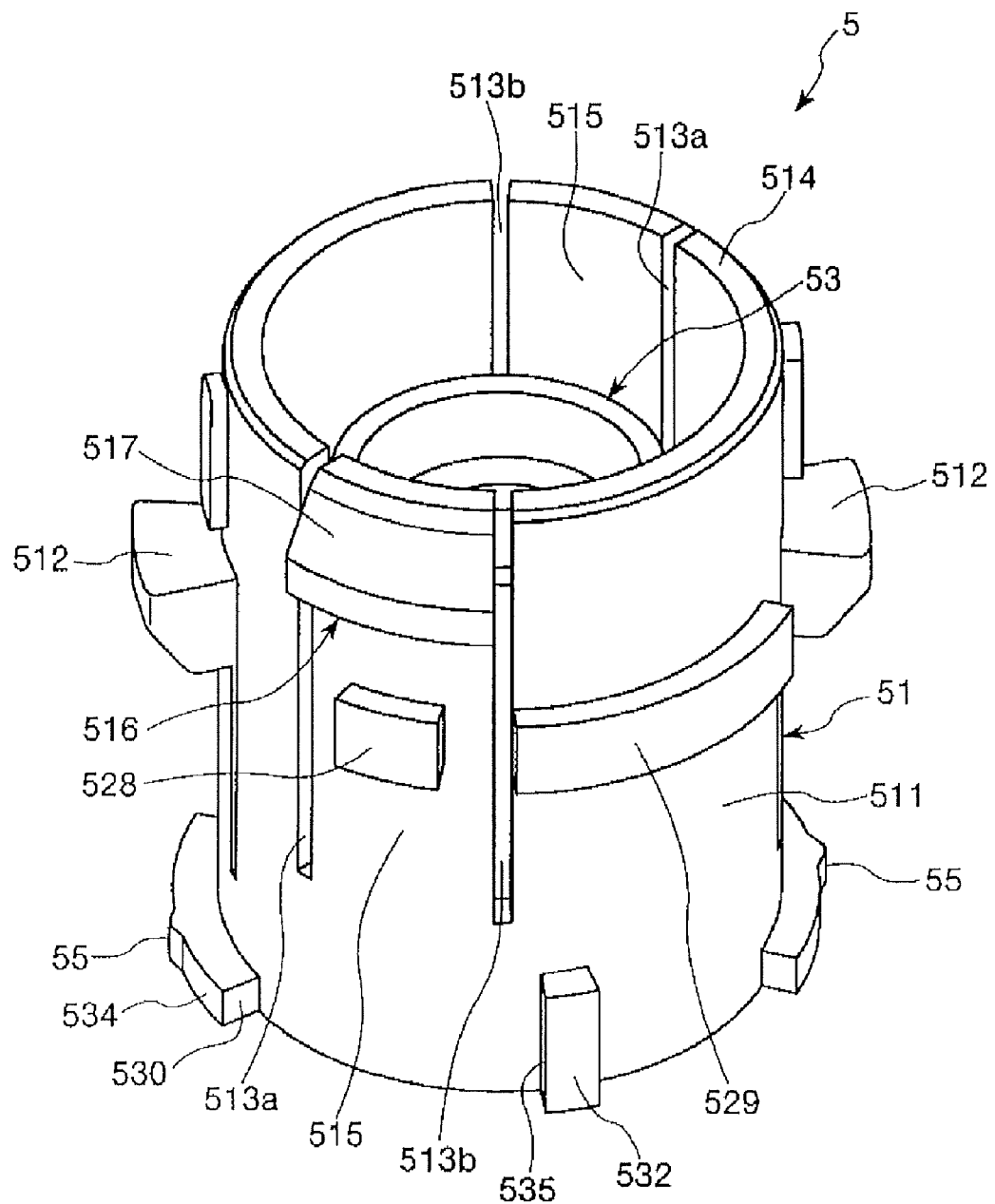
FIG. 13 is a perspective view showing an inner tube of the first connector shown in FIG. 11.
Figure 14:
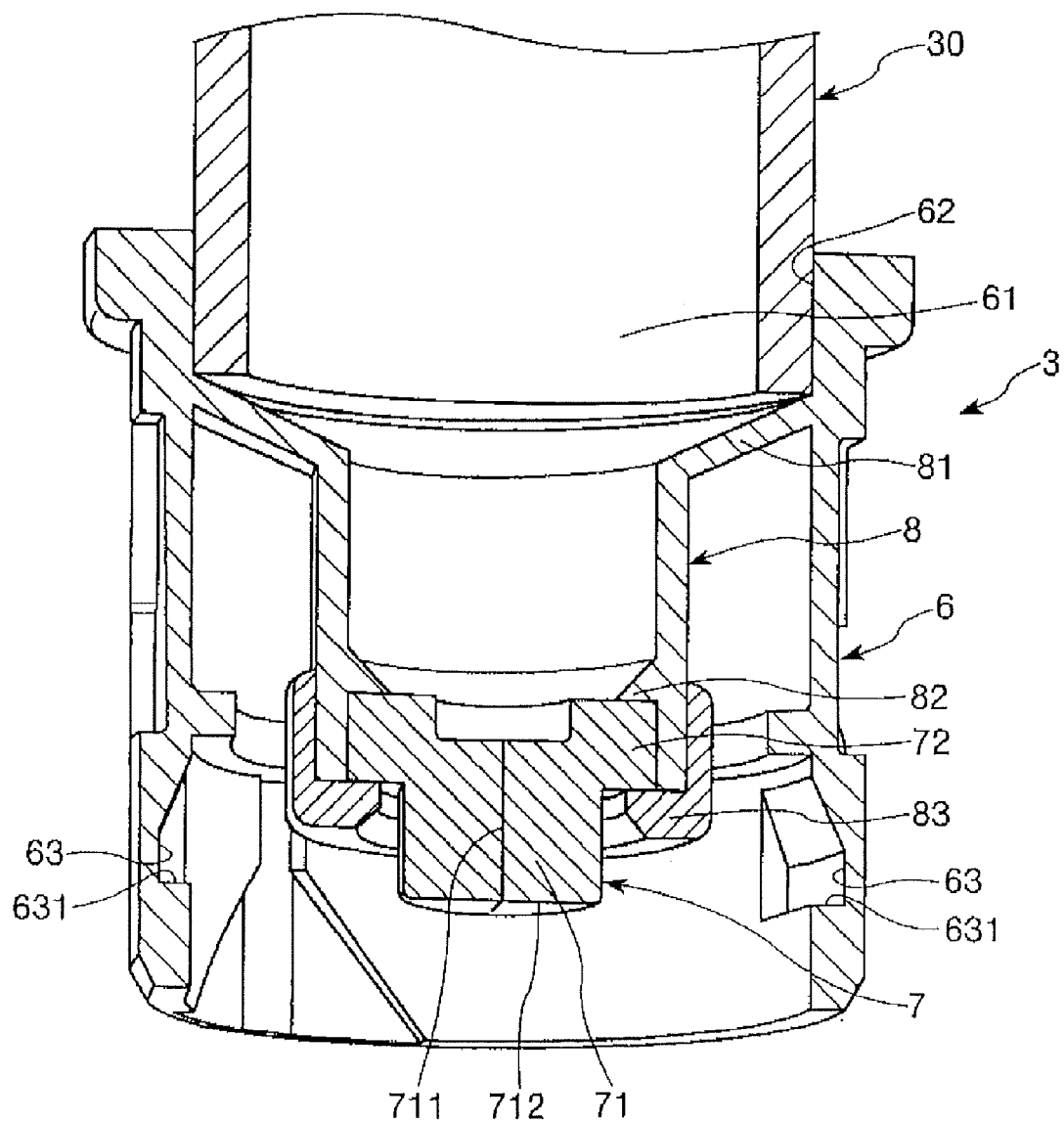
FIG. 14 is a vertical sectional perspective view showing a second connector in the connector assembly (first embodiment) of the present invention.

FIG. 1 is an exploded perspective view of a connector assembly (first embodiment) of the present invention; FIG. 2 is a perspective view illustrating a first state of the connector assembly (first embodiment) of the present invention; FIG. 3 is a sectional view taken along line A-A in FIG. 2; FIG. 4 is a sectional view taken along line B-B in FIG. 2; FIG. 5 is a sectional view taken along line C-C in FIG. 2; FIG. 6 is a perspective view illustrating a second state of the connector assembly (first embodiment) of the present invention; FIG. 7 is a sectional view taken along line D-D in FIG. 6; FIG. 8 is a sectional view taken along line E-E in FIG. 6; FIG. 9 is a perspective view illustrating a third state of the connector assembly (first embodiment) of the present invention; FIG. 10 is a sectional view taken along line F-F in FIG. 9; FIG. 11 is a vertical sectional perspective view showing a first connector in the connector assembly (first embodiment) of the present invention; FIG. 12 is a perspective view showing an outer tube of the first connector shown in FIG. 11; FIG. 13 is a perspective view showing an inner tube of the first connector shown in FIG. 11; FIG. 14 is a vertical sectional perspective view showing a second connector in the connector assembly (first embodiment) of the present invention; and FIG. 19 is a partial vertical sectional view showing a syringe to be connected to the first connector shown in FIG. 11. It is to be noted that, for the convenience of description, the upper side and the lower side in FIGS. 1 to 3, 6, 7, 9 to 11, 13 and 14 (similarly also in FIGS. 16 to 18) are hereinafter referred to as "distal end" and "proximal end," respectively, and the upper side and the lower side in FIG. 19 (similarly also in FIG. 15) are hereinafter referred to as "proximal end" and "distal end," respectively.

As shown in FIGS. 1 to 10, a connector assembly 1 has a first connector 2 and a second connector 3 which can be removably mounted on each other. As shown in FIG. 11, a syringe (liquid container) 20 is connected in advance to the first connector 2. As shown in FIG. 14, a tube 30 is connected in advance to the second connector 3. This connector assembly 1 is used to transfer, in an assembled state (state illustrated in FIGS. 2 to 10) in which the first connector 2 and the second connector 3 are assembled to each other, liquid from the first connector 2 side toward the second connector 3 side or in the opposite direction.

Before the constitution of the connector assembly 1 is described, a constitution of the syringe 20 connected to the first connector 2 of the connector assembly 1 and the tube 30 connected to the second connector 3 are described first.

As shown in FIG. 19, the syringe 20 in the present embodiment includes an outer tube (syringe outer tube) 201, a gasket 204 capable of slidably moving in the outer tube 201, and a pusher (plunger rod) 206 operable to move the gasket 204 along a longitudinal direction (axial direction) of the outer tube 201. The gasket 204 is connected to the distal end of the pusher 206.

The outer tube 201 is made up of a bottomed tubular member, and a reduced diameter portion (mouth portion) 202 having a diameter reduced from that of a body portion of the outer tube 201 is formed integrally so as to project at a central portion of the bottom portion on the distal end side of the outer tube 201.

Further, a lock adapter portion 210 disposed concentrically with the reduced diameter portion 202 is formed integrally with the outer tube 201 on the outer circumference side of the reduced diameter portion 202. The lock adapter portion 210 has a tubular shape and has a female thread 210a formed on an inner circumferential portion thereof. The female thread 210a can engage with a male thread 441 of the first connector 2 hereinafter described. By this threaded engagement, the syringe 20 and the first connector 2 can be connected to each other (refer to FIG. 11).

A flange (outer tube side flange) 203 is formed integrally so as to project on an outer circumference of a rear end of the outer tube 201.

Further, graduations for representing a liquid amount are applied to the outer circumferential face of the outer tube 201.

A material for the outer tube 201 includes various resins such as, for example, polyvinyl chloride, polyethylene, polypropylene, cyclic polyolefin, polystyrene, poly-(4-methylpentene-1), polycarbonate, acrylic resin, acrylonitrile-butadiene-styrene copolymer, polyester such as polyethylene terephthalate and polyethylene naphthalate, butadiene-styrene copolymer and polyamide (for example, nylon 6, nylon 6.6, nylon 6.10 and nylon 12). However, among them, such resins as polypropylene, cyclic polyolefin and polyester are preferable in that molding is easy and the water vapor permeability is low. It is to be noted that preferably the material for the outer tube 201 is substantially transparent in order to assure the visibility of the inside.

In such an outer tube 201 as described above, the gasket 204 made of an elastic material is disposed (inserted). A plurality of (two) ring-shaped projections are formed over the overall circumference on an outer circumferential portion of the gasket 204, and since the projections slidably move while closely contacting with the inner circumferential face of the outer tube 201, the liquid tightness can be assured with a higher degree of certainty and enhancement of the slidability is achieved.

Further, a hollow portion 205 which is open to a rear end face of the gasket 204 is formed in the gasket 204. A head portion 208 of the pusher 206 hereinafter described is screwed (fitted) into the hollow portion 205. A female thread is formed on the inner face of the hollow portion 205.

Although the material for the gasket 204 is not limited particularly, elastic materials such as various rubber materials such as, for example, natural rubber, butyl rubber, isoprene rubber, butadiene rubber, styrene-butadiene rubber and silicone rubber, various thermoplastic elastomers such as polyurethane-based, polyester-based, polyamide-based, olefin-based and styrene-based elastomers or mixtures of them can be used.

The pusher 206 has a bar-like main body portion 207 having a cross-shaped horizontal section.

On the distal end side of the main body portion 207, a head portion (connection portion) 208 for being inserted into the hollow portion 205 of the gasket 204 and connected to the gasket 204 is formed. A male thread capable of engaging with the female thread on the inner face of the hollow portion 205 is formed on an outer circumference of the head portion 208. By the threaded engagement of the male thread and the female thread, the gasket 204 and the pusher 206 are connected to each other. It is to be noted that the gasket 204 and the pusher 206 may have not a constitution wherein they are connected to each other by threaded engagement but another constitution wherein they are connected to each other by concave and convex fitting or the like, still another constitution wherein they are fixed to each other by adhesion, fusion or the like or yet another constitution wherein they are molded integrally.

Further, a disk-like (plate-like) flange 209 is formed at a rear end of the main body portion 207.

Further, as the material for the pusher 206, materials similar to those for the outer tube 201 described hereinabove can be used.

In the syringe 20 having such a constitution, a medical agent Q, for example, in the form of powder is contained in advance in a space 200 surrounded by the outer tube 201 and the gasket 204. It is to be noted that, although the medical agent Q is not limited particularly, the medical agent Q includes an agent which is dangerous if a medical care worker touches it by mistake, such as carcinostatics, immunosuppressants, etc., an agent which requires dissolution before use, such as an antibiotic, a hemostatic, etc., an agent which requires dilution, such as pediatric medical agents, an agent to be used over a plurality of times such as vaccine, heparin, pediatric medical agents and so forth.

A bag (not shown) which is filled in advance with the above-described dissolving liquid, is connected to the distal end side of the tube 30. Further, the second connector 3 is connected to a proximal end portion of the tube 30 (refer to FIG. 14). This tube 30 has flexibility and, as a material for the tube 30, for example, a soft resin material (elastic material) can be used. Although the soft resin material is not limited particularly, the soft resin material may include polyolefin such as polyethylene, polypropylene and ethylene-vinyl acetate copolymer, polyvinyl chloride, polybutadiene, polyamide, polyester, silicone and so forth. Among them, it is preferable to use polybutadiene particularly. Where polybutadiene is used as the material for the tube 30, it is superior in suitable flexibility, chemical resistance and anti-adsorption property of chemicals.

Now, the connector assembly 1 is described. As shown in FIGS. 1 to 10, the connector assembly 1 has a first connector 2 and a second connector 3. This connector assembly 1 can assume three states in its assembled state. The three states include a first state illustrated in FIG. 2 (similarly also in FIGS. 3 to 5), a second state illustrated in FIG. 6 (similarly also in FIGS. 7 and 8) and a third state illustrated in FIG. 9 (similarly also in FIG. 10). The second state is entered by rotating the second connector 3 around an axis of the second connector 3 (in a circumferential direction) with respect to the first connector 2 from the first state. The third state is entered by moving the first connector 2 and the second connector 3 toward each other from the second state.

As shown in FIG. 11, the first connector 2 has an outer tube 4 and an inner tube 5 arranged in the outer tube 4. Further, in the first connector 2, the inner tube 5 is rotatable around the axis of the outer tube 4 and movable along the axial direction of the outer tube 4.

As shown in FIGS. 11 and 12, the outer tube 4 includes an outer tube main body 41 having a bottomed tubular shape, and a hollow pin 42 provided concentrically with the outer tube main body 41 on the inner side of the outer tube main body 41.

As shown in FIG. 12, two (a pair of) groove portions (cam grooves (guide grooves)) 412 are formed in a wall portion (side wall) 411 of the outer tube main body 41. Those groove portions 412 are disposed at positions opposing to each other with the pin 42 interposed therebetween. A projection (cam follower) 512 of the inner tube 5 hereinafter described is inserted in and engaged with each of the groove portions 412 (refer to FIGS. 2, 6 and 9). It is to be noted that, since the groove portions 412 have the same constitution, one of the groove portions 412 is hereinafter described as a representative.

The groove portion 412 has an "L" shape as viewed in side elevation. More specifically, the groove portion 412 is composed of a circumferential groove (first transverse groove) 413 and an axial groove (longitudinal groove) 414 whose directions are different from each other (cross perpendicularly with each other). The circumferential groove 413 is formed along a circumferential direction of the wall portion 411. The axial groove 414 is formed along the axial direction of the wall portion 411 (outer tube main body 41). Further, the axial groove 414 extends from one end portion of the circumferential groove 413 toward the proximal end (toward the bottom portion 415 of the outer tube main body 41) and is communicated with the circumferential groove 413.

Meanwhile, the groove portion 412 is formed so as to extend through the wall portion 411 of the outer tube main body 41. While, in the present embodiment, an example wherein the groove portion 412 extends through the wall portion 411 is given, the groove portion 412 is not necessarily formed so as to extend through the wall portion 411.

Further, two elongated missing portions (grooves) 416a and 416b are formed at positions (between the groove portions 412) different from the groove portions 412 on the wall portion 411 of the outer tube main body 41 so as to face each other with the pin 42 interposed therebetween. The missing portions 416a and 416b are formed to extend along the axial direction from the distal end 417 of the outer tube main body 41. Consequently, a portion which has a rectangular shape (in the form of a small piece) and has elasticity, is formed between each of the missing portions 416a and each of the missing portions 416b. The portions function, in the first state, as pressing pieces (pressing portions) 418 for pressing elastic pieces 515 of the inner tube 5 hereinafter described toward the inner side of the inner tube 5 (toward the pin 42) (refer to, for example, FIG. 4). Since the pressing pieces 418 are formed from part of the wall portion 411 of the outer tube main body 41 in this manner, the constitution of the outer tube 4 is simplified in comparison with a constitution wherein the pressing pieces 418 are formed as members separate from the wall portion 411 of the outer tube main body 41.

On the outer side of each of the pressing pieces 418, operating pieces (operating portions) 43 for carrying out pressing operation of the pressing pieces 418 are provided. These operating pieces 43 have a width (length in the circumferential direction of the outer tube main body 41) greater than that of the pressing pieces 418. Since such operating pieces 43 are provided, when the pressing pieces 418 are operated for pressing, the operation can be carried readily and reliably.

The pin 42 is formed so as to project in a direction toward the distal end at a central portion of the bottom portion 415 of the outer tube main body 41. The pin 42 has a shape of a pipe and has a lumen which functions as a first flow path 421 through which liquid can pass. Further, the distal end 422 of the pin 42 forms a flat face perpendicular to the axis of the pin 42 (outer tube 4). A distal end portion of the pin 42 has a tapered shape whose outer diameter gradually decreases in a direction toward the distal end.

As shown in FIG. 11, a connecting portion 44 for being connected to the syringe 20 is provided at a central portion of the bottom portion 415 of the outer tube main body 41 on the opposite side to the pin 42. The connecting portion 44 has a shape of a pipe having a lumen which communicates with the lumen (first flow path 421) of the pin 42. Further, on an outer circumferential portion of the connecting portion 44, a male thread 441 is formed. The male thread 441 can be screwed into the female thread 210a of the lock adapter portion 210 of the syringe 20. By this, the syringe 20 and the first connector 2 (outer tube 4) are connected to each other reliably. Further, at this time, the mouth portion 202 of the syringe 20 is inserted into the connecting portion 44 and communicated with the first flow path 421.

It is to be noted that the material for the outer tube 4 is not limited particularly, and, for example, such materials as listed in the description of the outer tube 201 of the syringe 20 can be used.

As shown in FIG. 11, the inner tube 5 includes an inner tube main body 51 having a bottomed tubular shape, a first valve body 52 disposed on the inner side of the inner tube main body 51, and a supporting portion 53 for supporting the first valve body 52 on the inner tube main body 51.

As shown in FIG. 13, two (a pair of) projections 512 are formed so as to project toward the outside (outer side) on a wall portion (side wall) 511 of the inner tube main body 51. Those projections 512 are disposed at positions opposing to each other with the axis of the inner tube main body 51 interposed therebetween. As described hereinabove, the projections 512 can be individually inserted into and engaged with the groove portions 412 of the outer tube 4 (outer tube main body 41) (refer to FIGS. 2, 6 and 9). It is to be noted that, since the projections 512 have the same constitution, one of the projections 512 is described as a representative below.

The height of the projection 512 may have such a degree that it projects from the groove portion 412 or such a degree that it does not project from the groove portion 412. In the present embodiment, the height of the projection 512 has such a degree that it does not project from the groove portion 412 (refer to FIG. 4). The projection 512 prevents the inner tube 5 from disengaging from the outer tube 4 of the first connector 2.

Further, the projections 512 are exposed through the groove portions 412. Consequently, the position of the projection 512 with respect to the groove portion 412 can be visually confirmed, and consequently, it is possible to grasp whether the connector assembly in the assembled form is placed in the first state, the second state or the third state.

In the first state illustrated in FIGS. 2 and 4, the projections 512 are positioned at end portions of the circumferential grooves 413 of the groove portions 412 on the opposite side to the axial grooves 414. At this time, since base projection A-faces 530 (refer to FIG. 13) of the inner tube 5 are restricted by projection A-faces 481 (refer to FIG. 12) of the outer tube 4, the inner tube 5 cannot rotate in the counterclockwise direction in FIG. 4 with respect to the outer tube 4. Further, since base projection B-faces 534 (refer to FIG. 13) of the inner tube 5 are restricted by the projection D-faces 484 of the outer tube 4, the inner tube 5 cannot move in the downward direction in FIG. 2 with respect to the outer tube 4. Further, since the projections 512 are fitted in the groove portions 412 (this state is similar as in the succeeding second state), the inner tube 5 cannot move in the upward direction in FIG. 2 with respect to the outer tube 4.

In the second state illustrated in FIGS. 6 and 8, since A-faces 535 (refer to FIG. 13) of base longitudinal projections 532 of the inner tube 5 are restricted by projection B-faces 482 (refer to FIG. 12) of the outer tube 4 (this state is similar as in the succeeding third state), the inner tube 5 cannot rotate excessively in the clockwise direction in FIG. 4 with respect to the outer tube 4. At this time, the inner tube 5 is allowed to move in the downward direction in FIG. 2 with respect to the outer tube 4.

In the third state illustrated in FIG. 9, since the base projection A-faces 530 of the inner tube 5 are restricted by projection C-faces 483 (refer to FIG. 12) of the outer tube 4, the inner tube 5 cannot rotate in the counterclockwise direction in FIG. 4 with respect to the outer tube 4. Further, since the outer bottom face of a bottom portion 519 of the inner tube 5 is restricted by the bottom face on the inner side of the outer tube 4, the inner tube 5 cannot move excessively in the downward direction in FIG. 9 with respect to the outer tube 4.

As shown in FIG. 13, in the wall portion 511 of the inner tube main body 51, two pairs of elongated missing portions (grooves) 513a and 513b are formed at positions opposing to each other with the axis of the inner tube main body 51 interposed therebetween. Each of the missing portions 513a and 513b is formed along the axis direction from a distal end 514 of the inner tube main body 51. Consequently, between the missing portion 513a and the missing portion 513b, an elastic piece 515 having a rectangular shape (in the form of a small piece) and having elasticity is formed. As described hereinabove, in the first state, the elastic pieces 515 are pressed toward the inner side of the inner tube main body 51 by the pressing pieces 418 of the outer tube 4 and are deflected (deformed) in the direction. Further, if this pressing force is canceled, then the elastic pieces 515 restore their original shape by their own elasticity.

Further, a first engaging portion 516 is formed so as to project outwardly at an outer circumferential portion of a distal end of each of the elastic pieces 515. The first engaging portion 516 is a portion which engages with a second engaging portion 63 of the second connector 3 hereinafter described in the assembled state. As shown in FIG. 11, an inclined face 517 whose height gradually decreases in a direction toward the distal end is formed at a distal end portion of the first engaging portion 516. A proximal end face 518 of the first engaging portion 516 has a planar shape.

Since the elastic pieces 515 having such a constitution are formed, the first engaging portions 516 of the inner tube 5 can engage with the second engaging portions 63 of the second connector 3 in the assembled state. Further, as shown in FIGS. 3 and 4, in the first state, this engagement is maintained unless the operating pieces 43 of the outer tube 4 are operated to cause the pressing pieces 418 to press the elastic pieces 515 to such a degree that the elastic pieces 515 are deformed. In other words, it is impossible to release the engagement.

Furthermore, in order to release the engagement at a more accurate position, disconnection preventing portions 529 are provided on the outer circumferential portion of the inner tube 5 (refer to FIG. 13). More specifically, when the connector assembly 1 is in the proximity of the first state in which the release of the connection is not desired, even if small projections 528 are pressed by the pressing pieces 418 of the outer tube 4, the pressing pieces 418 contact with the disconnection preventing portions 529 to prevent deformation of the elastic pieces 515, and consequently, the connection is not released.

On the other hand, in any of the second state and the third state, the engagement between the first engaging portion 516 of the inner tube 5 and the second engaging portion 63 of the second connector 3 is maintained as shown in FIGS. 7 and 10.

In this manner, in all of the first state, second state and third state, the engagement (assembled state) of the first engaging portions 516 of the first connector 2 (inner tube 5) and the second engaging portion 63 of the second connector 3 is maintained. Consequently, when dissolving liquid (physiological salt solution) is supplied, for example, from the tube 30 to the syringe 20 through the connector assembly 1 in the assembled state, disassemble of the connector assembly 1 into the first connector 2 and the second connector 3 is prevented reliably. Consequently, transferring of the dissolving liquid can be carried out safely and reliably.

In the connector assembly 1, the first engaging portion 516 and the second engaging portion 63 can be regarded as locking means for connecting the first connector 2 (inner tube 5) and the second connector 3 (second connector main body 6). Further, the pressing pieces 418 can be regarded as unlocking means for releasing the connection between the first connector 2 and the second connector 3.

As shown in FIG. 11, the supporting portion 53 for supporting the first valve body 52 is provided at a central portion of the bottom portion 519 of the inner tube main body 51. Preferably, the supporting portion 53 has a shape of a pipe and is formed integrally with the inner tube main body 51 on the inner side of the inner tube main body 51. Further, the supporting portion 53 is disposed concentrically with the inner tube main body 51. The proximal end of the supporting portion 53 is opened to the bottom portion 519 of the inner tube main body 51.

A reduced diameter portion (stepped portion) 531 having a reduced inner diameter is provided on the inner circumferential portion of the supporting portion 53. The first valve body 52 is supported by the reduced diameter portion 531.

It is to be noted that, although the material for the inner tube main body 51 (including the supporting portion 53) is not limited particularly, for example, such materials as listed in the description regarding the outer tube 201 of the syringe 20 can be used.

As shown in FIG. 11, the first valve body 52 made of an elastic material is supported on the supporting portion 53. The first valve body 52 opens and closes the first flow path 421. This first valve body 52 has a columnar portion 521 having a columnar outer shape, and a flange portion 522 provided on an outer circumferential portion of the columnar portion 521.

The columnar portion 521 can be divided into a head portion 523 positioned on the distal end side thereof and a leg portion (insertion portion) 524 positioned on the proximal end side thereof. A columnar recess portion 525 is formed in the leg portion 524, and a distal end portion of the pin 42 positioned on the inner side of the supporting portion 53 (inner tube 5) is inserted (fitted) in the recess portion 525. A slit 526 extending through the head portion 523 in the axial direction (heightwise direction) is formed in the head portion 523. The slit 526 is communicated with the recess portion 525. This slit 526 is closed up, in the first state (refer to FIG. 3), the second state (refer to FIG. 7) and a natural state (refer to FIG. 11) in which no external force is applied, by the self-closing property of the first valve body 52. Consequently, the first flow path 421 is in a closed state. On the other hand, in the third state (refer to FIG. 10), the pin 42 is inserted through the slit 526 to open the slit 526. Consequently, the first flow path 421 is placed in an open state. It is to be noted that, while the slit 526 in the present embodiment has a straight-line shape, the shape of the slit 526 is not limited to this but may be, for example, a cross shape, a non-right angled "T" shape, a "Y" shape or a "T" shape.

The flange portion 522 is a portion positioned intermediately of the columnar portion 521 in the longitudinal direction and having an increased outer diameter. This flange portion 522 is sandwiched by the reduced diameter portion 531 of the supporting portion 53 and a ring-shaped member 54 of a ring shape fitted with the supporting portion 53. Consequently, the first valve body 52 is fixed reliably. While, in the present embodiment, the ring-shaped member 54 is used, the first valve body 52 may be fixed on the outer side of the reduced diameter portion 531 by a bonding agent without using the ring-shaped member 54.

As shown in FIG. 11, a packing 45 is installed between the inner circumferential portion of the supporting portion 53 of the inner tube 5 and the outer circumferential portion of the pin 42 of the outer tube 4. The packing 45 is a ring-shaped member having a semicircular cross sectional shape (horizontal sectional shape). It is to be noted that the packing 45 may not have a semicircular shape (arcuate shape) in advance but may assume a semicircular shape in a final state in which the packing of a circular shape or the like is assembled.

This packing 45 is inserted in a recess portion 423 formed in an outer circumferential portion of the pin 42 of the outer tube 4 along a circumferential direction of the pin 42. Consequently, the packing 45 can be prevented reliably from being displaced in a longitudinal direction with respect to the pin 42. Since such a packing 45 is installed, the liquid tightness (air tightness) of the first flow path 421 can be maintained reliably, and the dissolving liquid passing through the first flow path 421 is prevented reliably from leaking from the connector assembly 1 in the assembled state.

It is to be noted that the material for the first valve body 52 and the packing 45 is not limited particularly, and, for example, such materials as listed in the description of the gasket 204 of the syringe 20 can be used.

As shown in FIG. 14, the second connector 3 has a tubular second connector main body 6, a second valve body 7 disposed in the second connector main body 6, and a supporting portion 8 for supporting the second valve body 7 on the second connector main body 6.

The second connector main body 6 has a tubular shape and has a lumen which functions as a second flow path 61 through which liquid can pass. A distal end portion of the second connector main body 6 forms a tube connecting portion 62 into which a proximal end portion of the tube 30 can be inserted for connection. Further, the two second engaging portions 63 for engaging with the first engaging portions 516 of the inner tube 5 (inner tube main body 51) of the first connector 2 are provided on an inner circumferential portion of the second connector main body 6. It is to be noted that the number of second engaging portions 63 to be formed is not limited to two. Those second engaging portions 63 are disposed so as to face each other with an axis of the second connector main body 6 interposed therebetween. The second engaging portions 63 are individually formed in recess portions having a shape corresponding to the first engaging portions 516. As shown in FIG. 3, when the first engaging portions 516 and the second engaging portions 63 are engaged with each other (in the assembled state), proximal end faces 518 of the first engaging portion 516 and proximal end faces 631 of the second engaging portions 63 contact with each other to maintain the engagement state. In this manner, in the connector assembly 1, the first engaging portions 516 of the inner tube 5 and the second engaging portions 63 of the second connector main body 6 can be regarded as locking means for connecting the inner tube 5 (first connector 2) and the second connector main body 6 (second connector 3) to each other.

The supporting portion 8 is formed on the inner side of the second connector main body 6. Preferably, the supporting portion 8 and the second connector main body 6 are formed integrally with each other. The supporting portion 8 which supports the second valve body 7 is disposed concentrically with the second connector main body 6. This supporting portion 8 has a shape of a pipe and has an increased diameter at a distal end portion 81 thereof at which the supporting portion 8 is connected (coupled) to the inner circumferential portion of the second connector main body 6. Further, a reduced diameter portion (stepped portion) 82 having a reduced inner diameter is provided on the inner circumferential portion of the supporting portion 8. The second valve body 7 is supported by the reduced diameter portion 82.

It is to be noted that the material for the second connector main body 6 (including the supporting portion 8) is not limited particularly, and, for example, such materials as listed in the description of the outer tube 201 of the syringe 20 can be used.

The second valve body 7 made of an elastic material is supported on the supporting portion 8. The second valve body 7 opens and closes the second flow path 61. This second valve body 7 has a columnar portion 71 having a columnar outer shape, and a flange portion 72 provided on an outer circumferential portion of the columnar portion 71.

A slit 711 is formed in the columnar portion 71 such that it extends through the columnar portion 71 in an axial direction (heightwise direction) of the columnar portion 71. This slit 711 is closed up by the self-closing property of the second valve body 7 in the first state (refer to FIG. 3), the second state (refer to FIG. 7) and a natural state (refer to FIG. 14) in which no external force is applied. Consequently, the second flow path 61 is placed in a closed state. On the other hand, in the third state (refer to FIG. 10), the pin 42 is inserted through the slit 711 to open the slit 711. Consequently, the second flow path 61 is placed in an open state. It is to be noted that, while the slit 711 in the present embodiment has a straight-line shape, the shape of the slit 711 is not limited to this but may be, for example, a cross shape, a non-right angled "T" shape, a "Y" shape or a "T" shape.

The flange portion 72 is a portion which is positioned at a distal end portion of the columnar portion 71 and has an increased outer diameter. This flange portion 72 is sandwiched between the reduced diameter portion 82 of the supporting portion 8 and a ring-shaped member 83 in the form of a ring fitted with the supporting portion 8. By this, the second valve body 7 is fixed reliably. It is to be noted that the reduced diameter portion 82 and the second valve body 7 may be fixed to each other by a bonding agent without using the ring-shaped member 83.

It is to be noted that the material for the second valve body 7 is not limited particularly, and, for example, such materials as listed in the description of the gasket 204 of the syringe 20 can be used.

As described hereinabove, the connector assembly 1 in the assembled state can assume the first state, second state and third state. Now, the first state, second state and third state are described individually.

By moving the first connector 2 and the second connector 3 toward each other from a separate state (disassembled state) of the connector assembly 1 shown in FIG. 1, the connector assembly 1 is placed into the first state. It is to be noted that, in the first connector 2 in the separate state, the first flow path 421 is closed with the first valve body 52 (refer to FIG. 11). Further, in the first connector 2 in the separate state, the projections 512 of the inner tube 5 are positioned at end portions of the circumferential grooves 413 of the groove portions 412 of the outer tube 4 on the opposite side to the axial grooves 414 (refer to FIG. 1). Further, in the second connector 3 in the separate state, the second flow path 61 is closed with the second valve body 7 (refer to FIG. 14).

As shown in FIG. 3, in the first state, the first engaging portions 516 of the inner tube 5 of the first connector 2 and the second engaging portions 63 of the second connector 3 engage with each other as described hereinabove. By this, the inner tube 5 of the first connector 2 and the second connector 3 are connected to each other, and they can be operated to rotate jointly around the axis with respect to the outer tube 4 of the first connector 2. Further, in this first state, since the projections 512 of the inner tube 5 are positioned in the circumferential grooves 413 of the groove portions 412 of the outer tube 4, the inner tube 5 of the first connector 2 and the second connector 3 are prevented from moving in the axial direction of the outer tube 4.

Further, the connection between the inner tube 5 of the first connector 2 and the second connector 3 can be released by carrying out a pressing operation of the operating pieces 43 of the outer tube 4 of the first connector 2 toward the pin 42 in FIG. 4. More specifically, when the operating pieces 43 of the outer tube 4 of the first connector 2 are pressed toward the inner side of the outer tube 4 (toward the pin 42 in FIG. 4), the pressing pieces 418 press the elastic pieces 515 of the inner tube 5 facing the pressing pieces 418 toward the inner side. Consequently, the elastic pieces 515 are deformed toward the inner side, and the first engaging portions 516 formed on the elastic pieces 515 are separated away from the second engaging portions 63 of the second connector 3. Consequently, the connection between the inner tube 5 of the first connector 2 and the second connector 3 is released. In this manner, in the first state, unless a pressing operation for the operating pieces 43 is not carried out, the connection between the inner tube 5 of the first connector 2 and the second connector 3 is maintained.

Further, in the first state, the first flow path 421 is closed with the first valve body 52 and the second flow path 61 is closed with the second valve body 7, as in the separate state (refer to FIG. 3).

Further, as shown in FIG. 3, the first valve body 52 and the second valve body 7 are compressed in the axial direction with the end faces thereof pressing each other. Consequently, a distal end face 527 of the first valve body 52 and a proximal end face 712 of the second valve body 7 contact with each other liquid-tightly. Therefore, liquid passing through the connector assembly 1 in the assembled state can be prevented from leaking to the outside.

Further, as shown in FIG. 2, in the first connector 2, the projection 512 of the inner tube 5 is positioned at an end portion on the right side in FIG. 2 of the circumferential groove 413 of the groove portion 412 of the outer tube 4.

As shown in FIG. 5, inner tube side projections 55 and outer tube side projections 46 serving as blocking means for blocking the inner tube 5 from inadvertently rotating with respect to the outer tube 4 around the axis of the outer tube 4 in the first state are formed. As shown in FIGS. 5 and 13, the inner tube side projections 55 are formed so as to project on an outer circumferential portion of a proximal end of the inner tube main body 51. As shown in FIGS. 5 and 12, the outer tube side projections 46 are formed so as to project (so as to swell like a mountain) at positions corresponding (adjacent) to the inner tube side projections 55 in the first state on the inner circumferential portion of the outer tube main body 41. Since such inner tube side projections 55 and outer tube side projections 46 are formed, unless a rotating operation for the inner tube 5 of the first connector 2 is carried out, the inner tube 5 is prevented reliably from rotating and the first state is maintained reliably. Further, when the inner tube 5 of the first connector 2 and the second connector 3 are jointly rotated in the clockwise direction in FIG. 5 with respect to the outer tube 4 of the first connector 2, the inner tube side projections 55 ride over the outer tube side projections 46. Consequently, transition from the first state to the second state is allowed. It is to be noted that the inner tube side projections 55 and the outer tube side projections 46 may be provided at different places as long as the above object can be achieved.

Further, as shown in FIG. 1, first markers 47 and second markers 64 serving as positioning means for carrying out positioning of the inner tube 5 and the second connector 3 when the inner tube 5 of the first connector 2 and the second connector 3 are to be connected are provided. The first markers 47 are applied on the operating pieces 43 of the outer tube 4 of the first connector 2 (at positions corresponding to the first engaging portions of the inner tube 5), for example, by imprinting. Each first marker 47 is composed of an arrow mark which indicates a direction toward the distal end. The second markers 64 are applied on the outer circumferential portions of the second connector main body 6 at positions opposite to the second engaging portions 63, for example, by imprinting. Each second marker 64 is composed of an arrow mark which indicates a direction toward the proximal end. When the inner tube 5 of the first connector 2 and the second connector 3 are to be connected, by aligning (facing) the first markers 47 and the second markers 64 to each other, the connection operation can be carried out reliably.

As shown in FIG. 6, the connector assembly 1 is changed from the first state into the second state by rotating the inner tube 5 of the first connector 2 and the second connector 3 which are connected to each other, around the axis of the outer tube 4 with respect to the outer tube 4. When this rotating operation is carried out, the projection 512 of the inner tube 5 moves toward the left side in FIG. 6 along the circumferential groove 413 of the groove portion 412 of the outer tube 4. Consequently, the rotating operation can be carried out easily.

Further, in this second state, each of the projections 512 of the inner tube 5 is positioned at the intersection between the circumferential groove 413 and the axial groove 414. By this, the restriction of the movement of the inner tube 5 in the axial direction with respect to the outer tube 4 is released. Therefore, the inner tube 5 and the second connector 3 are allowed to move in the axial direction of the outer tube 4 with respect to the outer tube 4.

As shown in FIG. 8, when the inner tube 5 rotates around the axis of the outer tube 4 with respect to the outer tube 4 (in the second state), the elastic pieces 515 of the inner tube 5 are separated away from the pressing pieces 418, which press the elastic pieces 515, together with the rotation. In other words, the elastic pieces 515 are retracted to a position at which they are not pressed by the pressing pieces 418. Consequently, it becomes impossible to press the elastic pieces 515 with the pressing pieces 418 to release the engagement between the inner tube 5 (first engaging portion 516) and the second connector 3 (second engaging portion 63). Consequently, the connector assembly 1 in the assembled state can be prevented reliably from being separated inadvertently. Therefore, when the connector assembly 1 in the assembled state is used, flow of liquid from the distal end side to the proximal end side through the connector assembly 1 or in the opposite direction can be assured reliably.

Further, as described hereinabove, the lock adapter portion 210 of the syringe 20 is connected to the connecting portion 44 of the outer tube 4 of the first connector 2 by threaded engagement. The direction of rotation of the syringe 20 when the lock adapter portion 210 of the syringe 20 is to be connected to the connecting portion 44 of the outer tube 4, is opposite to the direction of rotation in which the inner tube 5 and the second connector main body 6 are rotated around the axis of the outer tube 4 with respect to the outer tube 4 upon transition from the first state to the second state. Consequently, when the inner tube 5 and the second connector main body 6 are rotated with respect to the outer tube 4, the threaded engagement between the connecting portion 44 of the outer tube 4 and the lock adapter portion 210 of the syringe 20 can be prevented reliably from being loosed (released). Therefore, during use of the connector assembly 1 in the assembled state, the syringe 20 is prevented from being inadvertently removed from the first connector 2.

As shown in FIG. 9, the connector assembly 1 is changed from the second state to the third state by moving the inner tube 5 of the first connector 2 and the second connector 3 which are connected to each other, in the direction toward the proximal end with respect to the outer tube 4 so as to approach thereto. When this moving operation is carried out, the projections 512 of the inner tube 5 move downwardly in FIG. 9 along the axial grooves 414 of the groove portions 412 of the outer tube 4. Consequently, the moving operation can be carried out easily.

Further, in the third state, the projections 512 of the inner tube 5 are positioned at the proximal end portions of the axial grooves 414.

As shown in FIG. 10, the pin 42 of the outer tube 4 is inserted through the slit 526 of the first valve body 52 of the inner tube 5 and the slit 711 of the second valve body 7 of the second connector 3. Consequently, in the third state, the first flow path 421 (lumen of the pin 42) of the first connector 2 and the second flow path 61 (lumen of the second connector main body 6) of the second connector 3 are communicated with each other. Through the first flow path 421 and the second flow path 61 communicated with each other, liquid can be transferred reliably from the first connector 2 side to the second connector 3 side or from the second connector 3 side to the first connector 2 side.

Further, as shown in FIG. 10, in the third state, the inner peripheral face of the slit 526 of the first valve body 52 of the inner tube 5 contacts closely with the outer circumferential face (outer circumferential portion) of the pin 42 of the outer tube 4 by elastic force of the first valve body 52. Similarly to this, the inner peripheral face of the slit 711 of the second valve body 7 of the second connector 3 contacts closely with the outer circumferential face of the pin 42 of the outer tube 4 by elastic force of the second valve body 7. Since, in the third state, the first valve body 52 and the second valve body 7 contact closely with the pin 42 of the outer tube 4 in this manner, the inner tube 5 of the first connector 2 and the second connector 3 which are connected to each other, is prevented reliably from inadvertently moving in a direction toward the distal end with respect to the outer tube 4, that is, the connector assembly 1 is prevented reliably from inadvertently returning to the second state. Further, also it is possible to control such inadvertent movement by resistance of the packing 45 installed between the inner circumferential portion of the supporting portion 53 of the inner tube 5 and the outer circumferential portion of the pin 42 of the outer tube 4. By this, the communication state (third state) between the first flow path 421 and the second flow path 61 is maintained, and transferring of liquid can be carried out reliably.

Further, in the third state, the elastic pieces 515 of the inner tube 5 remain retracted to the position at which they are not pressed by the pressing pieces 418 of the outer tube 4 which are adapted to press the elastic pieces 515. Consequently, as in the second embodiment, it is impossible to press the elastic pieces 515 with the pressing pieces 418 to release the engagement between the inner tube 5 and the second connector 3. Consequently, the connector assembly 1 in the assembled state can be prevented reliably from being inadvertently disassembled, and therefore, liquid can be transferred safely through the connector assembly 1.

Now, an example of a method of using the connector assembly 1 is described.

First, the first connector 2 to which a syringe 20 is connected and the second connector 3 to which a tube 30 is connected, are prepared.

The first connector 2 and the second connector 3 are moved toward each other (refer to FIG. 1) to connect the inner tube 5 of the first connector 2 and the second connector 3 to each other. Consequently, the connector assembly 1 is placed into the first state (refer to FIG. 2).

Then, the inner tube 5 of the first connector 2 and the second connector 3 are rotated around the axis of the outer tube 4 of the first connector 2 with respect to the outer tube 4. Consequently, the connector assembly 1 is placed into the second state (refer to FIG. 6).

Then, the inner tube 5 of the first connector 2 and the second connector 3 are pushed in a direction toward the proximal end with respect to the outer tube 4 of the first connector 2. Consequently, the connector assembly 1 is placed into the third state (refer to FIG. 9).

Then, the pusher 206 of the syringe 20 is pulled in the direction toward the proximal end. Consequently, the dissolving liquid in the bag connected in advance to the tube 30 is sucked into the syringe 20 through the tube 30 and the connector assembly 1. Then, the pusher 206 of the syringe 20 is moved back and forth, that is, subjected to a pumping operation. By this, the medical agent Q is dissolved uniformly in the dissolving liquid.

Then, the pusher 206 of the syringe 20 is placed into a state in which it is pulled in the direction toward the proximal end, and the connector assembly 1 is operated reversely to the above procedure to change the connector assembly 1 from the third state to the first state.

Then, the operating pieces 43 of the outer tube 4 of the first connector 2 are collectively pressed. Consequently, the connection between the inner tube 5 of the first connector 2 and the second connector 3 is released. Then, the first connector 2 and the second connector 3 are spaced away from each other.

Then, the first connector 2 is removed from the syringe 20, and the solution is administered from the syringe 20.

Second Embodiment

Figure 15:
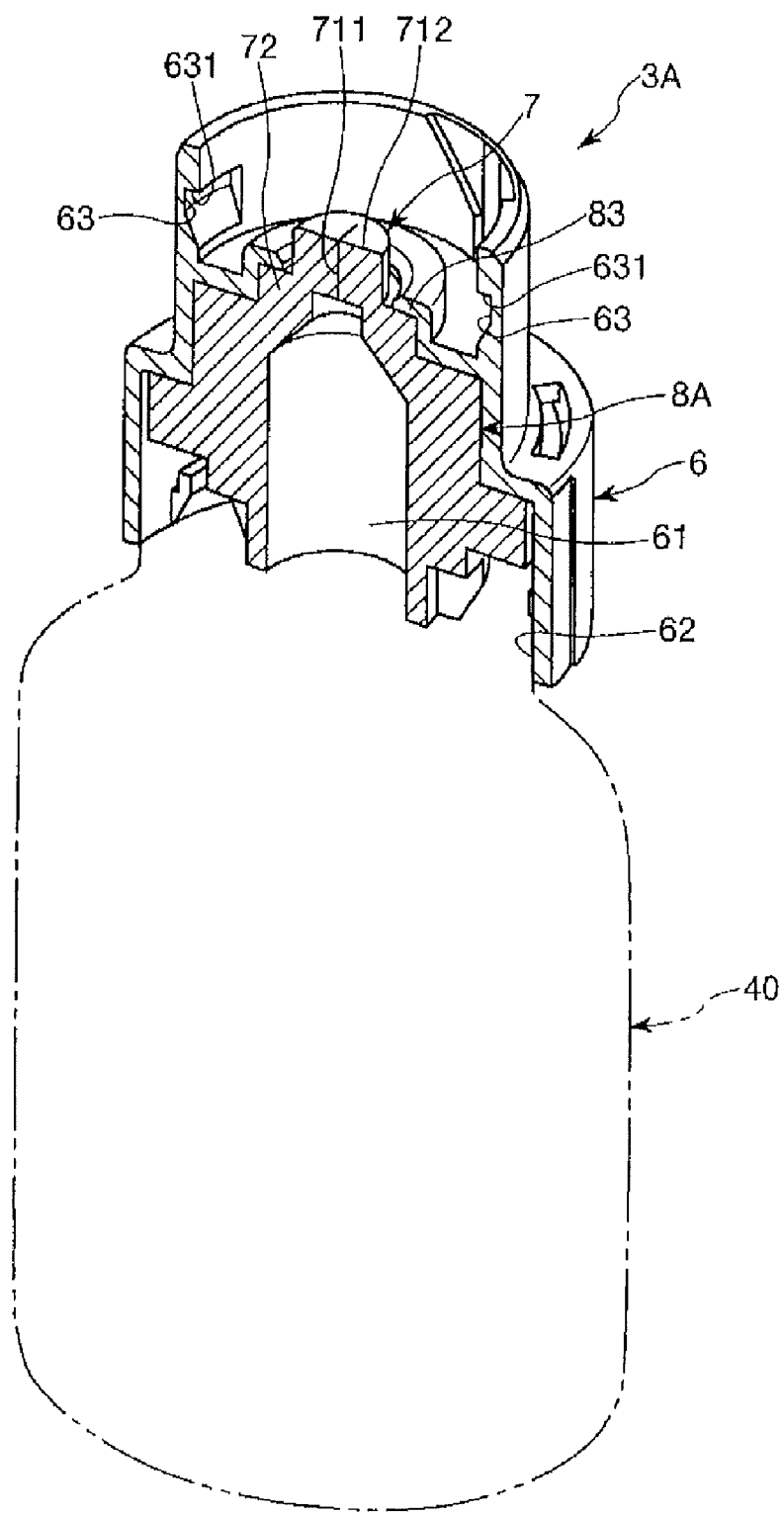
FIG. 15 is a vertical sectional perspective view showing a second connector in a connector assembly (second embodiment) of the present invention.

FIG. 15 is a longitudinal sectional perspective view showing a second connector in a connector assembly (second embodiment) of the present invention.

Although the second embodiment of the connector assembly of the present invention is described below with reference to this drawing, principally different points thereof from the embodiment described hereinabove are described while description of similar particulars is omitted.

The present embodiment is similar to the first embodiment except that the second connector is different in constitution therefrom.

The second connector 3A shown in FIG. 15 is mounted on a mouth portion of a vial (liquid container) 40 in which dissolving liquid can be contained. The vial 40 is a member which has a shape of a bottomed tube and has an end opening portion which is open at the distal end thereof. The distal end opening portion serves as a mouth portion of the vial 40.

In the second connector 3A, a supporting portion 8A is formed which supports the second valve body 7 on the second connector main body 6. It is to be noted that preferably the supporting portion 8A is formed integrally with the second valve body 7. The supporting portion 8A contacts, at an outer circumferential face thereof, closely (is pressed closely) with the inner circumferential face of the second connector main body 6. By this, the second valve body 7 can be supported on the second connector main body 6.

With the second connector 3A having such a constitution as described above, in the third state, the dissolving liquid can be sucked from the vial 40 into the syringe 20 through the connector assembly 1 in the assembled state.

Third Embodiment

Figure 16:
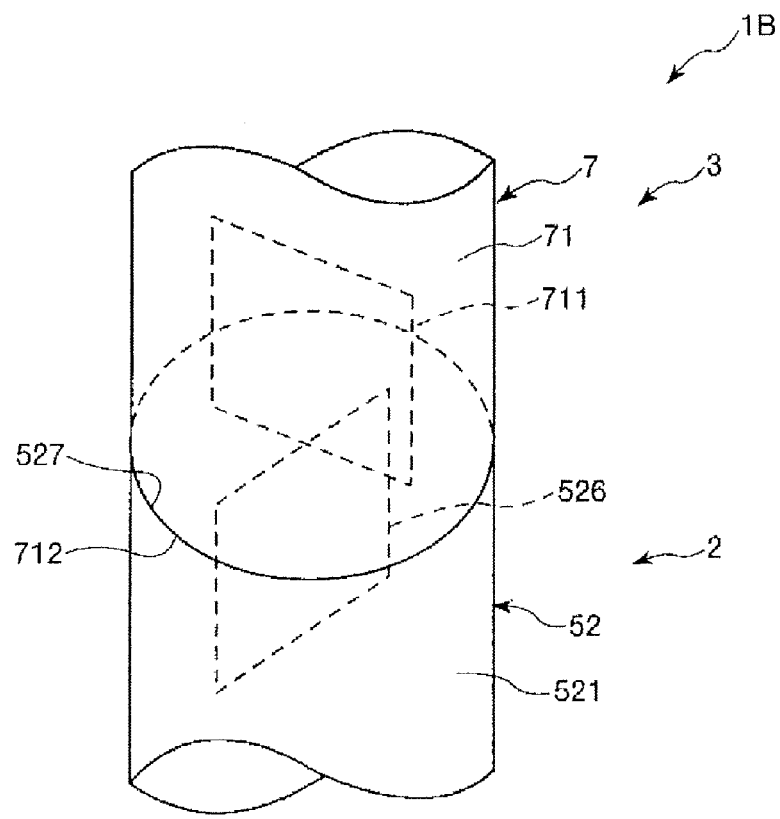
FIG. 16 is a perspective view showing a first valve body and a second valve body in a connector assembly (third embodiment) of the present invention.

FIG. 16 is a perspective view of a first valve body and a second valve body in a connector assembly (third embodiment) of the present invention.

Although the third embodiment of the connector assembly of the present invention is described below with reference to this drawing, principally different points thereof from the embodiments described hereinabove are described while description of similar particulars is omitted.

The present embodiment is similar to the first embodiment described hereinabove except the positional relationship between the slit of the first valve body and the slit of the second valve body in the assembled state.

As shown in FIG. 16, in the connector assembly 1B in the assembled state, the formation direction of the slit 526 of the first valve body 52 and the formation direction of the slit 711 of the second valve body 7 are not the same (do not align with each other) but cross perpendicularly with each other.

In the connector assembly 1B having such a constitution as just described, when the third state is entered, that is, when the pin 42 is inserted through the slit 526 of the first valve body 52 and the slit 711 of the second valve body 7, the liquid tightness in the proximity of the distal end face 527 of the first valve body 52 and the proximal end face 712 of the second valve body 7 is maintained reliably.

Fourth Embodiment

Figure 17:
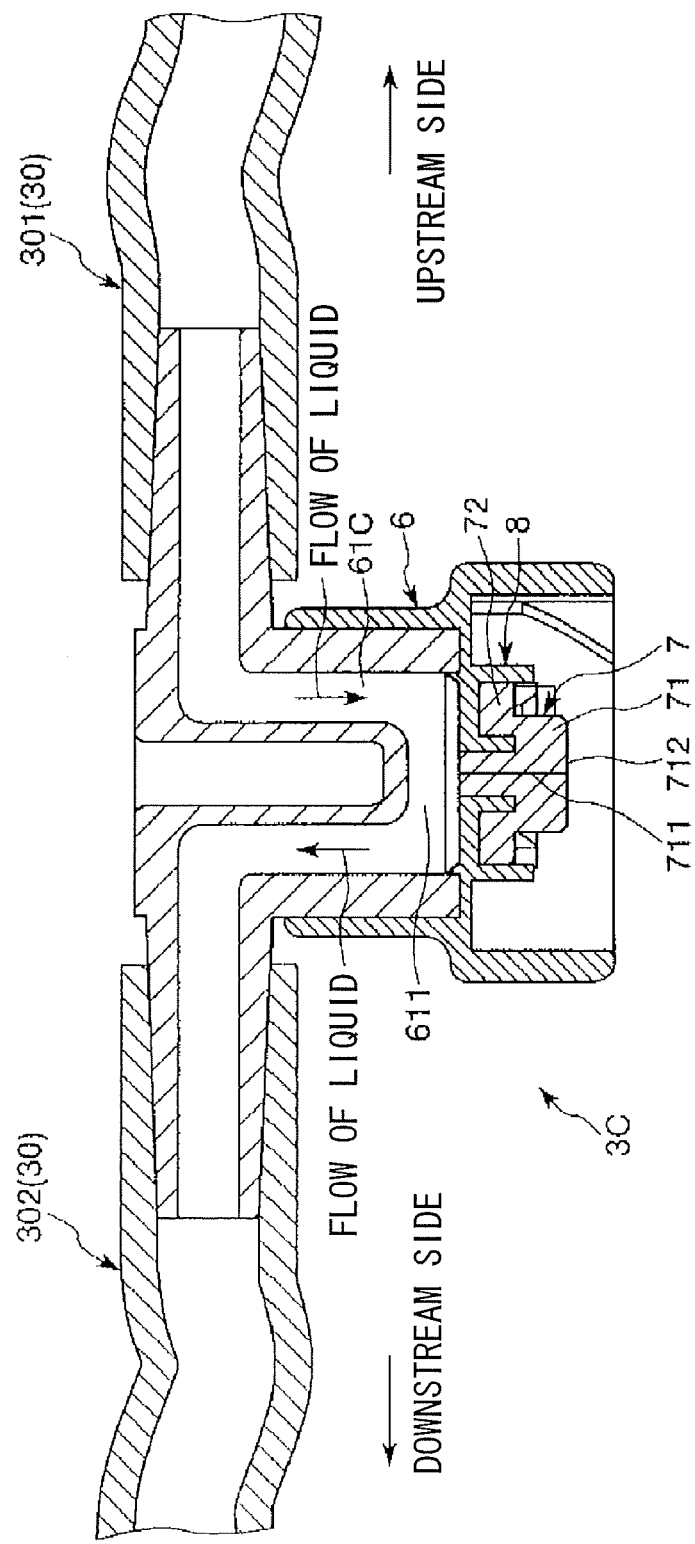
FIG. 17 is a vertical sectional view showing a second connector in a connector assembly (fourth embodiment) of the present invention.

FIG. 17 is a longitudinal sectional view showing a second connector in a connector assembly (fourth embodiment) of the present invention.

Although the fourth embodiment of the connector assembly of the present invention is described below with reference to this drawing, principally different points thereof from the embodiments described hereinabove are described while description of similar particulars is omitted.

The present embodiment is similar to the first embodiment described hereinabove except that the shape of the second flow path of the second connector is different.

The second connector C shown in FIG. 17 is installed intermediately of the tube 30 and is connected so as to bridge the space between a portion 301 on the upstream side and a portion 301 on the downstream side of the tube 30.

In this second connector C, a second flow path 61C is formed such that liquid flowing through the second flow path 61C reverses its flow direction in the proximity of the second valve body 7. More specifically, the second flow path 61C has a U-shaped portion 611 which has a "U" shaped longitudinal sectional shape in the proximity of the second valve body 7. Owing thereto, even if air bubbles exist in the liquid which passes through the second flow path 61C, they are prevented from remaining in the second flow path 61C.

Fifth Embodiment

Figure 18:
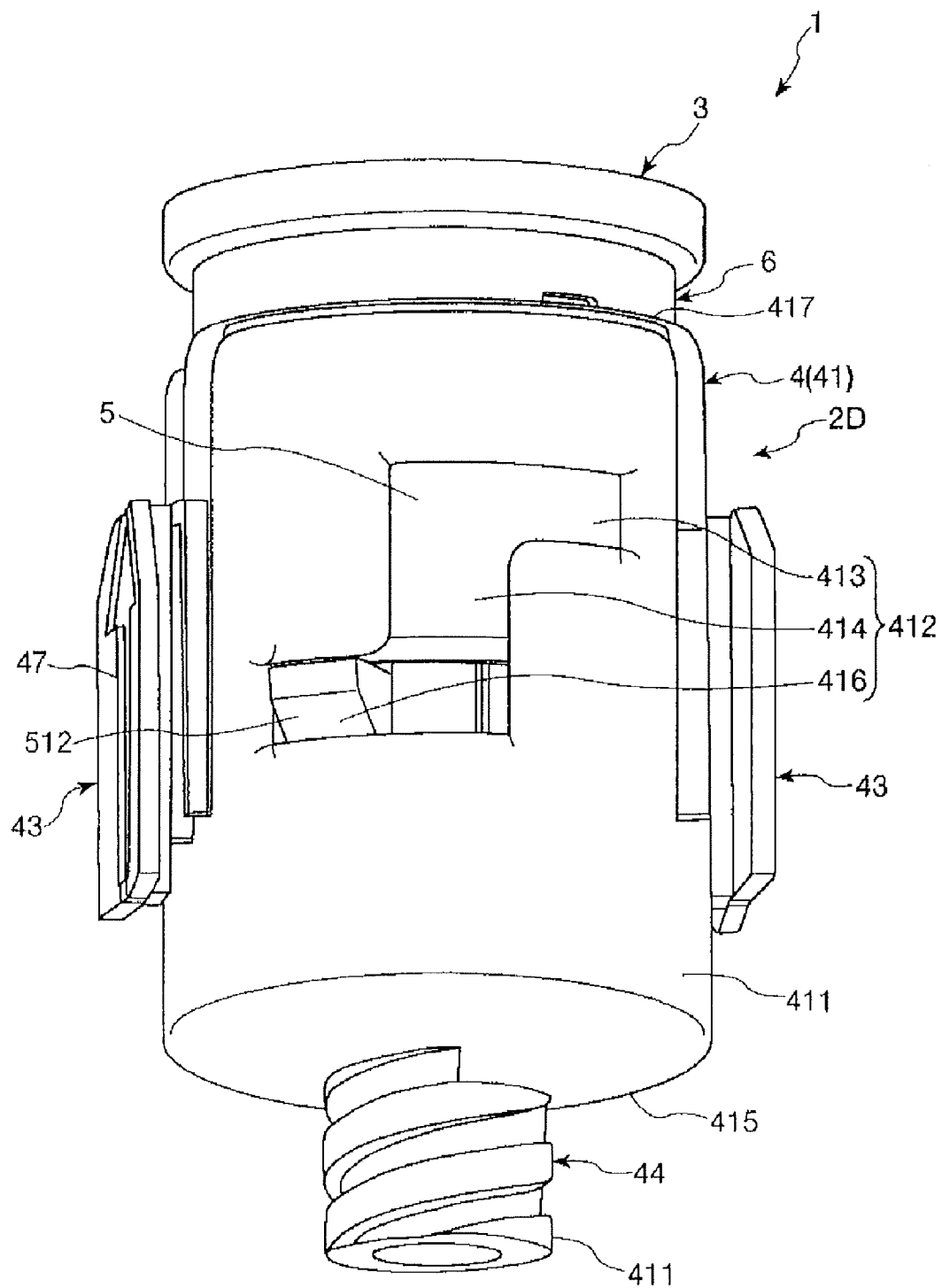
FIG. 18 is a perspective view showing a first connector in a connector assembly (fifth embodiment) of the present invention.
Figure 19:
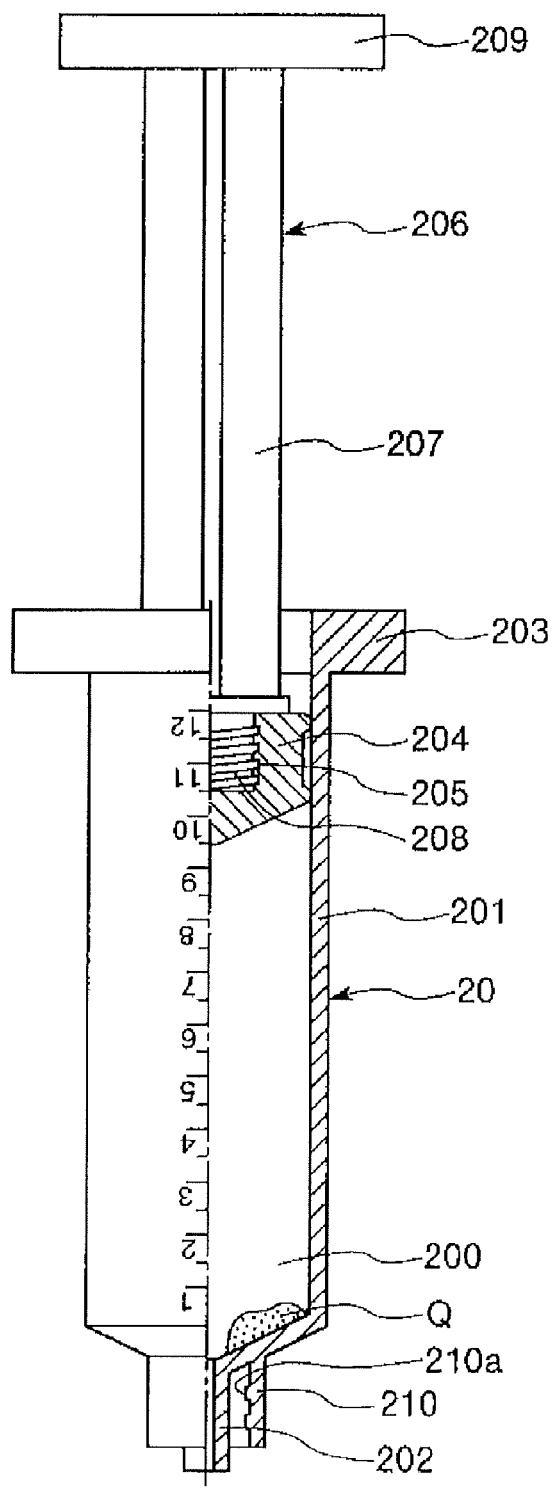
FIG. 19 is a partial vertical sectional view showing a syringe to be connected to the first connector shown in FIG. 11.

FIG. 18 is a perspective view showing a first connector in a connector assembly (fifth embodiment) of the present invention.

Although the fifth embodiment of the connector assembly of the present invention is described below with reference to this drawing, principally different points thereof from the embodiments described hereinabove are described while description of similar particulars is omitted.

The present embodiment is similar to the first embodiment described hereinabove except the constitution (shape) of the groove portion serving as a cam groove formed in the outer circumferential portion of the outer tube of the first connector.

In the first connector 2D shown in FIG. 18, the groove portions 412D formed in the outer tube 4 have a crank shape as viewed in side elevation. More specifically, each of the groove portions 412D further has, on the proximal end portion of the axial groove 414, a circumferential groove (second transverse groove) 416 communicating with the axial groove 414. In the groove portions 412D having such a constitution as just described, the projections 512 of the inner tube 5 can move. Accordingly, as shown in FIG. 18, in the connector assembly 1 in the third state, the projection 512 can be positioned at a left end portion of the circumferential groove 416 in FIG. 18. In this state, the inner tube 5 of the first connector 2D and the second connector 3 are prevented from moving in the axial direction of the outer tube 4 with respect to the outer tube 4.

By such a constitution as described above, for example, even if such force as to disassemble the first connector 2D and the second connector 3 from each other acts, the connectors are prevented from being disassembled from each other, and consequently, the assembled state (third state) of the connector assembly 1 is maintained reliably.

While the connector assembly of the present invention has been described in connection with the embodiments shown in the drawings, the present invention is not limited to this, and the components of the connector assembly can be replaced by those elements of an arbitrary constitution which can function similarly. Further, an arbitrary component or components may be added.

Further, the connector assembly of the present invention may be a combination of any two or more ones of the constitutions (features) of the embodiments described hereinabove.

Further, the pin of the first connector may be composed of a hollow needle which has a sharp needle end at a distal end thereof or may be composed of a hollow needle which has a needle end cut obliquely with respect to the axial direction. In this instance, the slit of the first valve body can be omitted. It is to be noted that the hollow needle may be made of a metal material or may be made of a resin material.

Further, while the first connector in the embodiments described above is constituted such that groove portions are formed in a wall portion of the outer tube and projections for being inserted into the groove portions are formed on a wall portion of the inner tube, the first connector is not limited to this, but may be constituted such that groove portions are formed in a wall portion of the inner tube while projections are formed on a wall portion of the outer tube.

Further, although two groove portions and two projections are provided on the first connector in the embodiments, the present invention is not limited in this respect. One groove portion and one projection may be provided on the first connector.

Further, although each of the first valve body and the second valve body has a slit formed thereon, they are not limited to this. The first valve body and the second valve body each may have, for example, a fine hole (pinhole) formed therein.

INDUSTRIAL APPLICABILITY

A connector assembly of the present invention includes a first connector having an outer tube having a tubular shape and including a hollow pin having a lumen provided in the inner side thereof and functioning as a first flow path through which liquid can pass, and an inner tube having a tubular shape and including a first valve body made of an elastic material for opening and closing the first flow path, the inner tube being disposed for rotation around an axis thereof in the outer tube and for movement along the direction of the axis, a second connector including a tubular second connector main body having a lumen which functions as a second flow path through which liquid can pass, and a second valve body disposed in the second connector main body and made of an elastic material for opening and closing the second flow path, locking means for connecting the inner tube and the second connector main body in an assembled state in which the first connector and the second connector are assembled, and unlocking means for releasing the connection between the inner tube and the second connector main body by the locking means, wherein the assembled state includes a first state in which the inner tube and the second connector main body are connected by the locking means, and the inner tube and the second connector main body are rotatable around the axis of the outer tube with respect to the outer tube but are not movable in an axial direction while the first flow path is closed by the first valve body and the second flow path is closed by the second valve body, a second state which is established by rotating the inner tube and the second connector main body around the axis of the outer tube with respect to the outer tube from the first state, and in which the inner tube and the second connector main body are movable in the axial direction with respect to the outer tube, and a third state which is established by moving the inner tube and the second connector main body in the axial direction with respect to the outer tube from the second state so as to approach thereto, and in which the pin is inserted through the first valve body and the second valve body to communicate the first flow path and the second flow path with each other, and wherein the connection between the inner tube and the second connector main body by the locking means is capable of being released by the unlocking means when the connector assembly is in the first state, whereas the connection is not capable of being released by the unlocking means when the connector assembly is in any of the second state and the third state. Therefore, liquid can be transferred safely and reliably from the first connector side to the second connector side or in the opposite direction. Accordingly, the connector assembly of the present invention has industrial applicability.

The invention claimed is:

1. A connector assembly, comprising:
a first connector having an outer tube having a tubular shape and including a hollow pin having a lumen provided in an inner side thereof and functioning as a first flow path through which liquid can pass, and an inner tube having a tubular shape and including a first valve body made of an elastic material for opening and closing the first flow path, the inner tube being disposed for rotation around an axis thereof in the outer tube and for movement along the direction of the axis;
a second connector including a tubular second connector main body having a lumen which functions as a second flow path through which liquid can pass, and a second valve body disposed in the second connector main body and made of an elastic material for opening and closing the second flow path;
locking means for connecting the inner tube and the second connector main body in an assembled state in which the first connector and the second connector are assembled; and
unlocking means for releasing the connection between the inner tube and the second connector main body by the locking means,
wherein the assembled state includes:
a first state in which the inner tube and the second connector main body are connected by the locking means, and the inner tube and the second connector main body are rotatable around an axis of the outer tube with respect to the outer tube but are not movable in an axial direction while the first flow path is closed by the first valve body and the second flow path is closed by the second valve body;
a second state which is established by rotating the inner tube and the second connector main body around the axis of the outer tube with respect to the outer tube from the first state, and in which the inner tube and the second connector main body are movable in the axial direction with respect to the outer tube; and
a third state which is established by moving the inner tube and the second connector main body in the axial direction with respect to the outer tube from the second state so as to approach thereto, and in which the pin is inserted through the first valve body and the second valve body to communicate the first flow path and the second flow path with each other,
wherein the connection between the inner tube and the second connector main body by the locking means is capable of being released by the unlocking means when the connector assembly is in the first state, whereas the connection is not capable of being released by the unlocking means when the connector assembly is in any of the second state and the third state,
wherein the connector assembly further comprises blocking means for blocking inadvertent rotation of the inner tube with respect to the outer tube around the axis of the outer tube when the connector assembly is in the first state,
wherein the locking means comprises a first engaging portion provided on an outer circumferential portion of the inner tube and a second engaging portion provided on an inner circumferential portion of the second connector main body for engaging with the first engaging portion,
wherein the first engaging portion is formed of an elastic piece that is elastically deformable inward, and
wherein the unlocking means comprises a pressing piece provided on the outer tube which, when pressed inward against the elastic piece, causes the first engagement portion to be separated away from the second engagement portion.

2. The connector assembly according to claim 1, wherein a wall portion of one of the outer tube and the inner tube has a groove portion formed therein and having a first transverse groove formed along a circumferential direction thereof and a longitudinal groove formed along an axial direction thereof and communicating with the first transverse groove while a wall portion of the other of the outer tube and the inner tube has a projection formed so as to project thereon and inserted in the groove portion such that the projection moves along the first transverse groove when the inner tube rotates around the axis thereof with respect to the outer tube and such that the projection moves along the longitudinal groove when the inner tube moves along the axial direction thereof with respect to the outer tube.

3. The connector assembly according to claim 2, wherein, when the connector assembly is in the first state, the projection is positioned at an end portion of the first transverse groove on the opposite side of the longitudinal groove, and when the connector assembly is in the second state, the projection is positioned at an intersection between the first transverse groove and the longitudinal groove, whereas when the connector assembly is in the third state, the projection is positioned at an end portion of the longitudinal groove on the opposite side of the first transverse groove.

4. The connector assembly according to claim 2, wherein the first transverse groove communicates with a distal end of the longitudinal groove and a second transverse groove is provided to communicate with a proximal end of the longitudinal groove, and wherein by rotating the inner tube and the second connector with respect to the outer tube around the axis of the outer tube, the projection moves to a position within the second transverse groove in the third state.

5. The connector assembly according to claim 1, wherein each of the first valve body and the second valve body has a portion of a columnar shape, and end faces of the portions closely contact liquid-tightly with each other in the assembly state.

6. The connector assembly according to claim 1, wherein each of the first valve body and the second valve body has a portion of a columnar shape and having a slit formed therein so as to extend therethrough in the axial direction.

7. The connector assembly according to claim 1, wherein the blocking means is formed of an inner tube side projection of the inner tube and an outer tube side projection of the outer tube.

8. The connector assembly according to claim 1, wherein the outer tube has a connecting portion to be connected, by threaded engagement, to a liquid container in which liquid can be contained, and a direction of rotation of the liquid container when the liquid container is to be connected to the outer tube, is opposite to a direction of rotation in which the inner tube and the second connector main body rotate around the axis with respect to the outer tube upon transition from the first state to the second state.

9. The connector assembly according to claim 1, wherein the pin is positioned on an inner side of the inner tube, and a ring-shaped packing made of an elastic material is disposed between an outer circumferential portion of the pin and an inner circumferential portion of the inner tube.

10. The connector assembly according to claim 1, wherein the second flow path has a U-shaped portion in a vicinity of the second valve body, the U-shaped portion having a U-shape in a longitudinal cross section, and wherein a liquid in the second flow path flowing toward the second valve body reverses in the vicinity of the second valve body to flow away from the second valve body through the U-shaped portion.

* * * * *